US007845601B1

(12) United States Patent
Culpepper et al.

(10) Patent No.: US 7,845,601 B1
(45) Date of Patent: Dec. 7, 2010

(54) MEDICAL EQUIPMENT TRANSPORT SYSTEM

(75) Inventors: Taylor C. Culpepper, Oklahoma City, OK (US); Marcus J. Brown, Edmond, OK (US); James J. Walker, Brownsville, TX (US); John R. Pierson, Guthrie, OK (US); Travis W. Webb, Tuttle, OK (US); James A. Walker, Oklahoma City, OK (US)

(73) Assignee: Modular Services Company, Oklahoma City, OK (US)

( * ) Notice: Subject to any disclaimer, the term of this patent is extended or adjusted under 35 U.S.C. 154(b) by 868 days.

(21) Appl. No.: 11/558,099

(22) Filed: Nov. 9, 2006

(51) Int. Cl.
*A47F 5/00* (2006.01)
(52) U.S. Cl. ............. 248/125.2; 248/125.8; 248/176.1; 248/911; 248/912; 280/35; 5/600
(58) Field of Classification Search .................. 248/544, 248/558, 121, 125.8, 125.2, 176.1, 911, 912; 280/35; 5/600
See application file for complete search history.

(56) References Cited

U.S. PATENT DOCUMENTS

| 2,696,963 | A |   | 12/1954 | Shepherd |
| 3,931,452 | A |   | 1/1976 | Nilsson |
| 4,023,771 | A | * | 5/1977 | Walchek ..................... 249/139 |
| 4,190,224 | A |   | 2/1980 | LeBlanc et al. |
| 4,511,157 | A |   | 4/1985 | Wilt, Jr. |
| 4,572,536 | A |   | 2/1986 | Doughty |
| 4,795,122 | A |   | 1/1989 | Petre |
| 4,831,673 | A |   | 5/1989 | Winckler |
| 4,879,798 | A | * | 11/1989 | Petre ............................ 29/434 |
| 4,901,967 | A | * | 2/1990 | Petre ........................... 248/327 |
| 4,945,592 | A |   | 8/1990 | Sims et al. |

(Continued)

FOREIGN PATENT DOCUMENTS

CA        2392270        9/2003

(Continued)

OTHER PUBLICATIONS

Getinge USA, Inc., "Ceiling Pendant Systems for the ICU," commercial literature dated 2004 (Getinge USA, Inc., Rochester, NY USA).

(Continued)

*Primary Examiner*—J. Allen Shriver, II
*Assistant Examiner*—Bradley H Duckworth
(74) *Attorney, Agent, or Firm*—Mary M. Lee

(57) ABSTRACT

A medical equipment transport system for supporting medical equipment while a patient is transported. The system comprises an equipment rack, such as an IV stand. While in the hospital room, the rack is mounted on a bracket supported on a mobile tower. When the patient is moved, the rack is transferred to a similar bracket on the bed. Transfer of the rack between bed and tower brackets is accomplished using a lift mechanism in the tower. The lift mechanism includes a bogie stabilized by radially-arranged bearings, enabling the tower to accept omni directional loading and moment forces. The rack is supported on each of the brackets by two vertically-aligned conical pins nested in tapered bushings, providing additional stability. A self-locking, self-releasing latch assembly prevents inadvertent dislocation of the rack. A customized adapter enables attachment of the bracket to any model bed without structurally altering it, simplifying installation and preserving warranties.

39 Claims, 19 Drawing Sheets

U.S. PATENT DOCUMENTS

| | | | |
|---|---|---|---|
| 4,957,121 A | 9/1990 | Icenogle et al. | |
| 5,005,233 A | 4/1991 | Toivio et al. | |
| 5,040,765 A | 8/1991 | Schonfelder | |
| 5,077,843 A | 1/1992 | Foster et al. | |
| 5,117,521 A | 6/1992 | Foster et al. | |
| 5,135,191 A | 8/1992 | Schmuhl | |
| 5,247,962 A | 9/1993 | Walker | |
| 5,275,364 A | 1/1994 | Burger et al. | |
| 5,299,659 A | 4/1994 | Imbeault et al. | |
| 5,306,109 A | 4/1994 | Kreuzer et al. | |
| 5,319,816 A | 6/1994 | Ruehl | |
| 5,337,992 A | 8/1994 | Pryor et al. | |
| 5,358,205 A | 10/1994 | Starkey et al. | |
| 5,400,995 A | 3/1995 | Boyd | |
| 5,412,272 A | 5/1995 | Mensching | |
| 5,448,859 A | 9/1995 | Walker et al. | |
| 5,457,831 A | 10/1995 | Foster et al. | |
| 5,513,406 A | 5/1996 | Foster et al. | |
| 5,527,125 A * | 6/1996 | Kreuzer et al. | 403/325 |
| 5,527,289 A | 6/1996 | Foster et al. | |
| 5,562,091 A | 10/1996 | Foster et al. | |
| 5,577,279 A | 11/1996 | Foster et al. | |
| 5,618,090 A | 4/1997 | Montague et al. | |
| 5,644,876 A | 7/1997 | Walker | |
| 5,647,491 A | 7/1997 | Foster et al. | |
| 5,680,661 A | 10/1997 | Foster et al. | |
| 5,704,577 A | 1/1998 | Gordon | |
| 5,737,782 A | 4/1998 | Matsuura et al. | |
| 5,876,016 A | 3/1999 | Urban et al. | |
| 5,890,687 A | 4/1999 | Pryor et al. | |
| 5,898,961 A | 5/1999 | Ambach et al. | |
| 5,924,658 A | 7/1999 | Shiery et al. | |
| 5,966,760 A | 10/1999 | Gallant et al. | |
| 5,987,670 A | 11/1999 | Sims et al. | |
| 6,056,249 A | 5/2000 | Fillon, Jr. | |
| 6,073,285 A | 6/2000 | Ambach et al. | |
| 6,079,678 A | 6/2000 | Schott et al. | |
| 6,089,518 A | 7/2000 | Nilsson | |
| 6,179,260 B1 | 1/2001 | Ohanian | |
| 6,182,662 B1 | 2/2001 | McGhee | |
| 6,213,481 B1 * | 4/2001 | Marchese et al. | 280/35 |
| 6,231,016 B1 | 5/2001 | Slone | |
| D443,365 S | 6/2001 | Walker | |
| 6,256,935 B1 | 7/2001 | Walker | |
| 6,269,594 B1 | 8/2001 | Walker | |
| D452,573 S | 12/2001 | Walker | |
| 6,343,601 B1 | 2/2002 | Kiske et al. | |
| D472,325 S | 3/2003 | Walker | |
| 6,619,599 B2 | 9/2003 | Elliott et al. | |
| 6,668,493 B1 | 12/2003 | Walker | |
| 6,694,548 B2 | 2/2004 | Foster et al. | |
| 6,725,474 B2 | 4/2004 | Foster et al. | |
| 6,817,585 B2 | 11/2004 | Wagner et al. | |
| 6,830,421 B1 | 12/2004 | Broderick | |
| 6,834,840 B1 | 12/2004 | Metz et al. | |
| 6,966,086 B2 | 11/2005 | Metz et al. | |
| 6,993,799 B2 | 2/2006 | Foster et al. | |
| 7,008,269 B2 | 3/2006 | Riley et al. | |
| 7,040,057 B2 | 5/2006 | Gallant et al. | |
| 7,065,811 B2 | 6/2006 | Newkirk et al. | |
| 7,065,812 B2 | 6/2006 | Newkirk et al. | |
| 7,073,765 B2 | 7/2006 | Newkirk | |
| 7,204,714 B2 | 4/2007 | Walker et al. | |
| 7,216,382 B2 | 5/2007 | Newkirk et al. | |
| 7,219,472 B2 | 5/2007 | Gallant et al. | |
| 7,254,850 B2 | 8/2007 | Newkirk et al. | |
| 7,278,615 B2 | 10/2007 | Schubert et al. | |
| 7,549,893 B1 | 6/2009 | Walker et al. | |
| 2003/0014817 A1 | 1/2003 | Gallant et al. | |
| 2003/0177713 A1 | 9/2003 | Walker et al. | |
| 2004/0164220 A1 | 8/2004 | Newkirk | |
| 2004/0231248 A1 | 11/2004 | Walker et al. | |
| 2004/0237202 A1 | 12/2004 | Gallant et al. | |
| 2005/0000019 A1 | 1/2005 | Newkirk et al. | |
| 2006/0179571 A1 | 8/2006 | Newkirk | |
| 2006/0207025 A1 | 9/2006 | Newkirk et al. | |
| 2006/0207026 A1 | 9/2006 | Newkirk et al. | |
| 2006/0226333 A1 | 10/2006 | Newkirk | |
| 2007/0068089 A1 | 3/2007 | Gallant et al. | |
| 2007/0176063 A1 | 8/2007 | Heimbrock et al. | |

FOREIGN PATENT DOCUMENTS

| | | |
|---|---|---|
| CA | 2467300 A1 | 11/2004 |
| EP | 0219274 A2 | 4/1987 |
| GB | 1476061 | 6/1977 |
| MX | PA/A/2004/004613 A | 8/2005 |
| MX | 262578 | 11/2008 |
| WO | PCT/NL97/00356 A1 | 12/1997 |
| WO | PCT/US99/18405 A1 | 2/2000 |

OTHER PUBLICATIONS

Hill-Rom Services Inc., "Hill-Rom Infusion Management Device (IMD)," commercial literature dated Oct. 2, 2007 (Hill-Rom Services, Inc., Wilmington, DE, USA).

Modular Services Company, "Stratus Modular Medical Headwall System—Owners Manual and Installation Instructions," commercial literature, Jun. 1, 2005 (Modular Services Company, Oklahoma City, OK, USA).

* cited by examiner

MEDICAL EQUIPMENT TRANSPORT SYSTEM

FIELD OF THE INVENTION

The present invention relates to devices for supporting medical equipment while transporting a patient on a hospital bed, gurney or other patient transport device.

DETAILED DESCRIPTION OF THE PREFERRED EMBODIMENT

As medical technology advances, the number and type of medical equipment and therapeutic devices needed at the patient's bedside likewise increases. Equipment and devices commonly used at a patient's bedside include but are not limited to intravenous infusion containers and infusion pumps, cardiac monitors, oxygen delivery devices, and defibrillators. These items of equipment must be maintained in close proximity to the patient and to each other primarily because of the limitations imposed by the length of electronic lead wires and plastic tubing. This close proximity must be maintained not only when the patient is settled in a hospital room, but also during transportation within the hospital or other medical facility, such as when the patient is moved to and from surgery, the radiology department, or for other treatment or diagnostic procedures.

Transportation of critically ill patients presents the challenge of maintaining the close proximity of the required medical equipment without discomfort or injury to the patient and without damage to the equipment. The present invention provides a medical equipment transport system that meets this challenge and offers many advantages.

This system includes a medical equipment rack designed to support a wide variety of medical devices and equipment. While the patient remains in the hospital room, the rack can be supported on a bracket mounted on a bedside stand or tower. For transport, the rack is transferred to a bracket mounted on the hospital bed. The rack is supported by a pair of conical pins that nest in a pair of plastic bushings. This provides a self-centering function removing the need for precise alignment of the rack to the brackets. The use of two vertically spaced-apart pins provides stability for the rack.

The rack is transferred to and from the brackets by means of lift mechanism in the tower. A bogie is mounted inside the housing by a radially oriented bearing assembly that accepts load and moment forces in any direction. The bogie is raised and lowered by an actuator, such as a screw drive, which may be driven by an electric motor conveniently controlled by a switch on the top of the tower. Inadvertent dislodgement of the rack from the brackets is prevented by a self-locking and self-releasing latch assembly; no manual operation of the latch assembly is required either to lock it or release it. The bracket fixed to the bed is mounted by means of an adapter customized for the specific make and model of the bed. Thus, no structural modification of the bed is required to use this transport system, which means that the installation is simple and will not void warranties on the bed.

Figure 1:
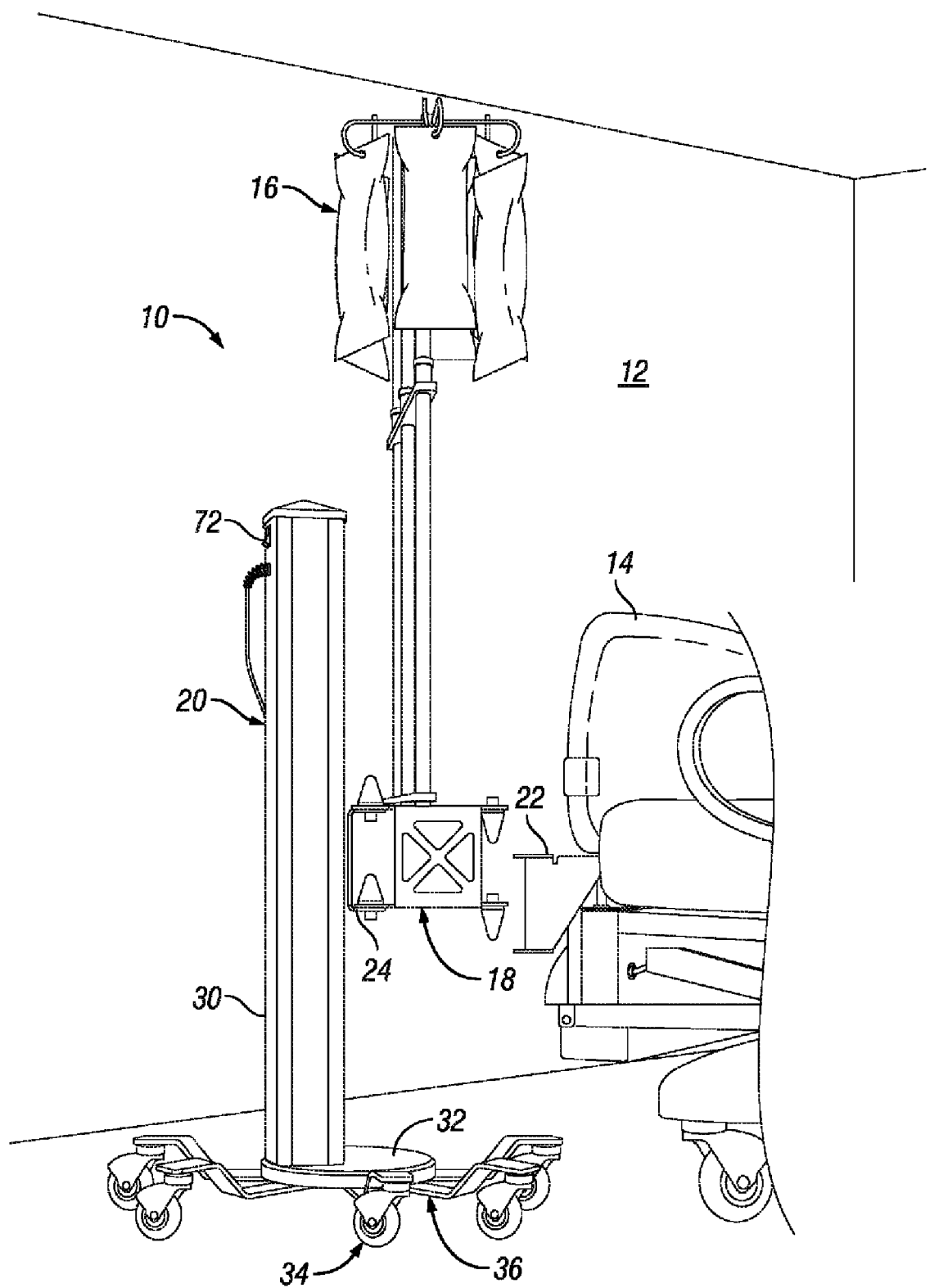
FIG. 1 is a perspective view of a medical equipment transport system constructed in accordance with a preferred embodiment of the present invention and shown in a hospital room adjacent a hospital bed. The equipment rack is mounted on the tower for use while the patient is in the hospital room.

Turning now to the drawings in general and to FIG. 1 in particular, there is shown therein a medical equipment transport system constructed in accordance with the present invention and designated generally by the reference numeral 10. As is apparent from FIG. 1, the system 10 is ideally suited for use in a hospital room 12 and is depicted adjacent a hospital bed 14. However, the system 10 is useful in any setting in which patients require transport with accompanying medical equipment designated generally at 16. For example, the system 10 will be equally useful in clinics, emergency rooms, operating rooms, nursing homes, and virtually any sort of medical treatment facility. Similarly, while the system 10 is shown with a hospital bed 14, the system may be adapted readily for use with other patient transport devices, such as gurneys, examining tables, wheelchairs, and the like.

Figure 2:
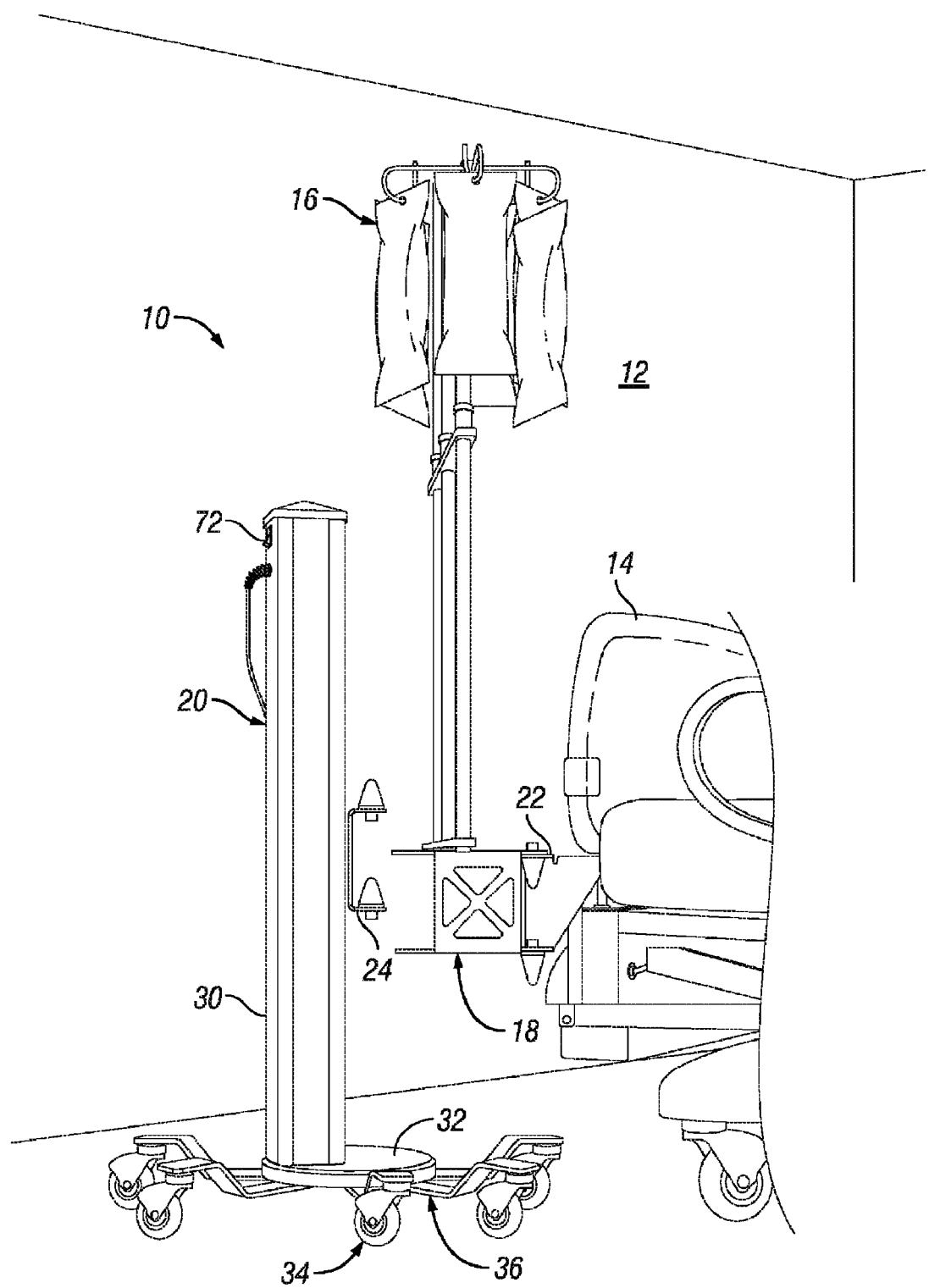
FIG. 2 is a perspective view of the medical equipment transport system of FIG. 1. The equipment rack has been transferred to the bed bracket for transport.

As seen in FIG. 1, the system 10 generally comprises four main components, an equipment rack 18, a stand or tower 20 for supporting the rack in the room 12, a first bracket 22 for supporting the rack 18 on the bed 14, and a second bracket 24 for supporting the rack on the tower. While the patient remains in the hospital room 12, the rack 18 usually will be supported on the second bracket 24 on the tower 20 as this allows medical personnel easy access to the patient from all sides of the bed. The tower 20 preferably comprises a vertically oriented housing 30 supported on a base 32. To facilitate easy repositioning of the tower around the bed 14, the base 32 is mobile. In the preferred embodiment, the base is supported on rollers designated generally at 34, which may be supported on radially extending legs designated generally at 36 for stability. In a manner to be described in detail hereafter, the rack 18 is transferred to the first bracket 22 on the bed 14 during transport of the patient, as illustrated in FIG. 2.

Figure 3:
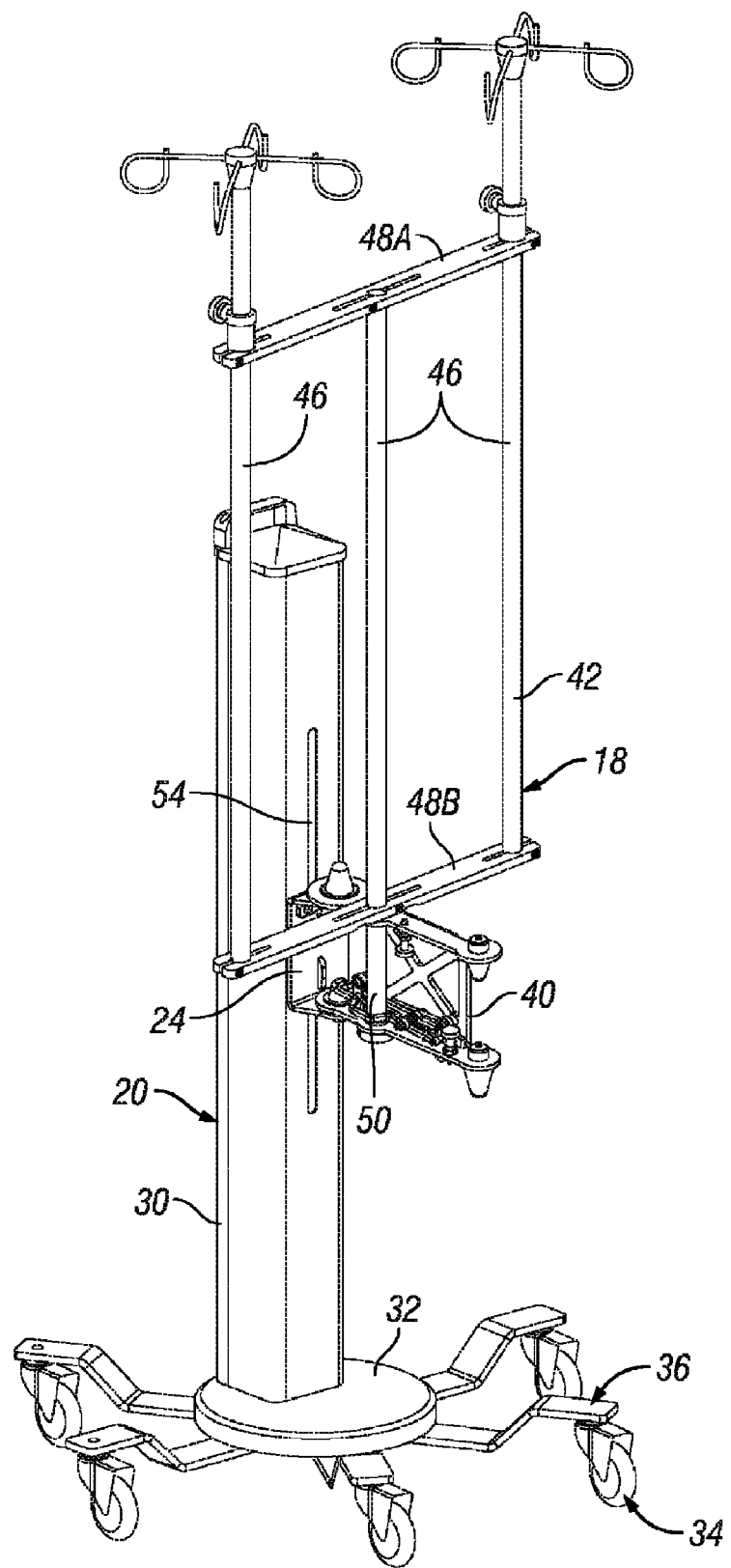
FIG. 3 is a perspective view of another side of the medical equipment transport system showing the configuration of a preferred equipment rack and the slot on the side of the tower along which the mounting bracket travels.

With reference to FIG. 3, a preferred equipment rack 18 will be described. As used herein, "rack" means any framework, stand, or grating or other support on or in which any type of medical equipment can be supported. In the embodiment shown, the rack 18 comprises a base 40 and a post assembly 42. The base 40 includes the bed-to-tower transfer mechanism and latch assembly that will be described later. The post assembly 42 supports the medical equipment 16 (FIGS. 1 & 2). Since the type of medical equipment 16 varies widely, the configuration of the rack 18 may also vary. In the present embodiment, the post assembly 42 comprises a plurality of vertical posts 46 stabilized by horizontal bars, such as an upper bar 48A and a lower bar 48B. Preferably, the post assembly 42 is removably and pivotally supported on the base 40. To that end, the center post 46 has a lower section or extension 50 that is journaled in the base 40 as explained below.

As indicated previously, the transfer of the rack 18 between the bed bracket 22 and tower bracket 24 is accomplished by a lift mechanism in the tower 20. More specifically, with reference now also to FIG. 4, the lift mechanism raises and lowers the tower bracket 24, which connects to a bogie 52 inside the housing 30 and travels along a slot 54 (FIG. 3) in one side of the housing.

As will be readily appreciated, there are many suitable types of drive assemblies that could be adapted driving the vertical movement of the bogie 52. In most cases, it will be preferred to employ a drive assembly that translates rotary motion into linear motion, such as a screw drive actuator. More preferably, a ball drive is utilized. A suitable actuator is model number 85262 ball drive actuator from Motion Systems Corporation (Eatontown, N.J.). This drive assembly, designated generally at 58, comprises a motor 60, a 10:1 gearbox 62, and a ball screw 64 and ball nut 66.

Electrical wiring for the motor 60 is supplied through a junction box 70 at the top of the tower 20. The power cord 62 is conveniently stored on the side of the housing 30, and operation of the motor 60 is controlled by a switch 72 (see also FIGS. 1 & 2) near the top of the housing.

Although the above-described drive assembly is motor-driven, a hand crank could be substituted. Further, in lieu of a screw drive, other types of drive systems could be used, such pneumatic or hydraulic lifts, pulleys, chain drives, and rack and pinion assemblies. In addition, although an electric motor is shown herein, other types of motors could be employed instead, such as pneumatic or hydraulic motors.

Figure 5:
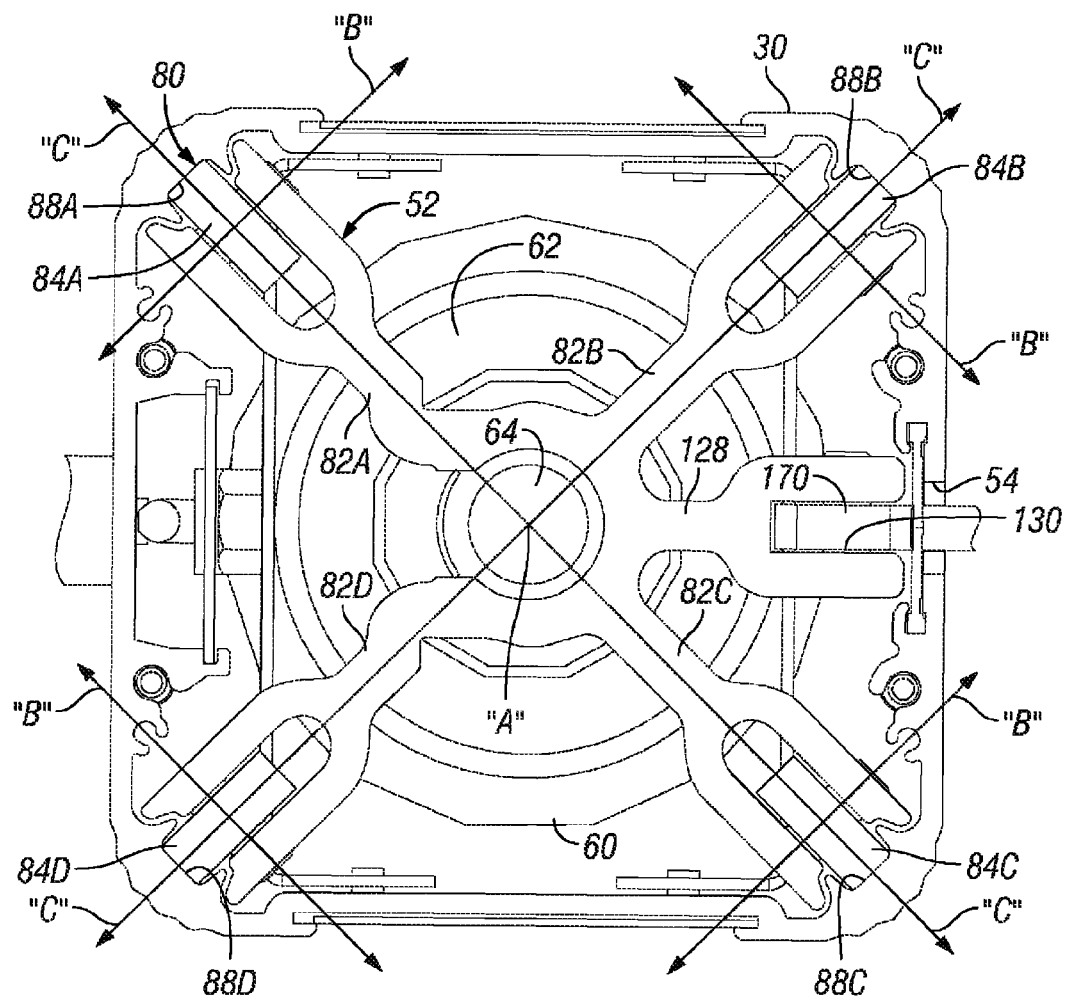
FIG. 5 is a sectional view through the tower above the level of the carrier or bogie and rack frame support bracket taken along line 5-5 of FIG. 4.

With continuing reference to FIG. 5 and referring also to FIGS. 6 and 7, the preferred configuration for the bogie 52 will be explained. As is seen best in FIG. 5, the housing 30 forms a bearing frame for supporting the bogie 52 as it moves vertically on the screw 64. In this embodiment, the housing 30 itself forms the bearing frame. It will be understood, however, that a bearing frame could be provided by one or more separate structures inside the housing. As FIG. 5 illustrates, the screw 64 is coaxial with a central longitudinal or vertical axis "A" of the housing 30. Thus, the screw 64 supports the bogie 52 for vertical movement inside the housing (bearing frame) 30.

A bearing assembly 80 is provided between the bearing frame/housing 30 and the bogie 52. Preferably, the bearing assembly 80 comprises at least three bearings, and more preferably four bearings, positioned radially equidistantly around the central longitudinal axis "A". As used herein, "radially" or "radially oriented" in reference to the bearing assembly refers to a bearing interface that defines a plane that is perpendicular to a line extending radially from the central axis of the bearing frame/housing 30.

Figure 4:
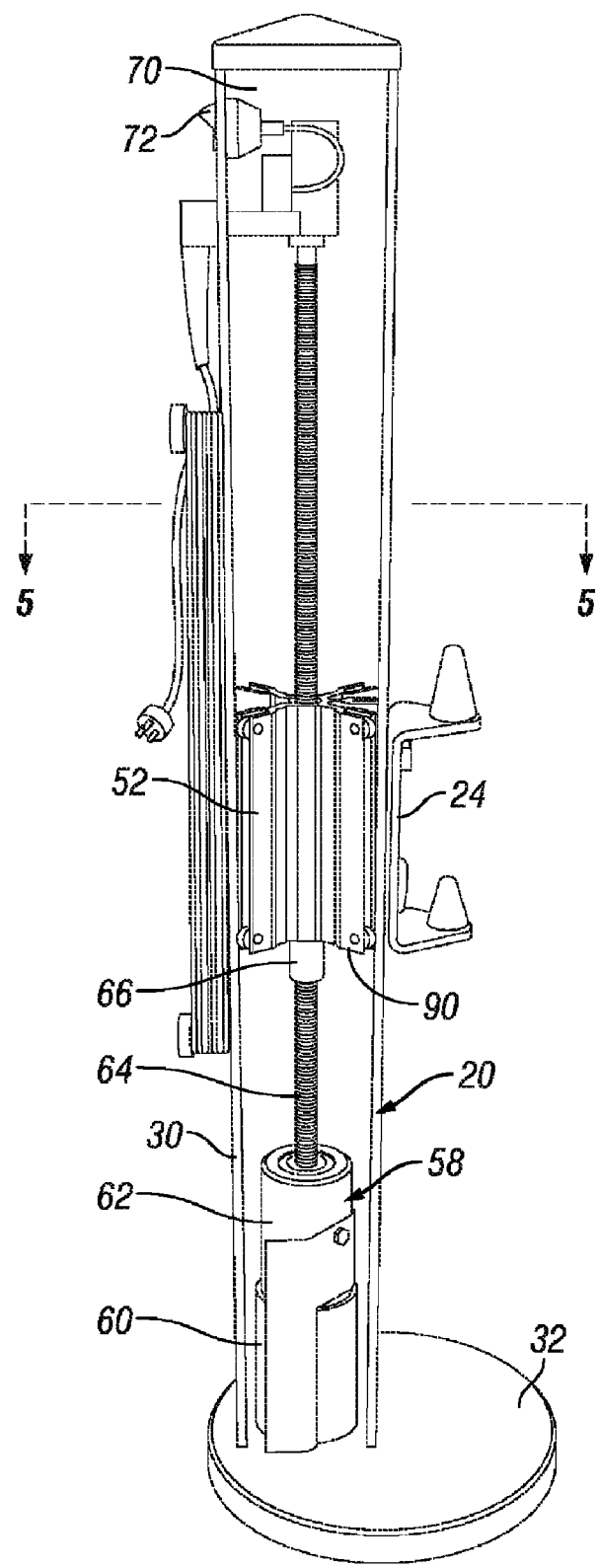
FIG. 4 is a side elevational view of the tower with the side panel removed to show the linear actuator and junction box inside.

This is exemplified in the preferred configuration. As seen in FIGS. 5-7, the bogie 52 is a extrusion forming four spokes 82A-82D, and the bearings 84A-84D, comprise cylindrical roller bearings rotatably supported on the end of each of the spokes. The bearing frame/housing 30 defines four corresponding vertically-oriented bearing races 88A-88D disposed equidistantly about the central axis "A". Thus, each of the bearings 84A-84D is supported for vertical movement along one of the races 88A-88D as the bogie 52 moves vertically in the housing/frame 30. As seen in FIGS. 6 and 7, the bogie 52 preferably is elongated vertically, so that two or more tiers of bearings can be supported thereon, that is, two more bearings vertically aligned on each spoke 82A-82D. As best seen in FIGS. 4 and 6, the ball nut 66 is threadedly received in the lower or bottom end 90 of the bogie 52 and is provided with internal threads 92 (FIG. 6) to engage the screw 64.

Referring again to FIG. 5, it will be apparent now that the axis of rotation "B" of each bearing is perpendicular to a line "C" extending radially from the central axis "A" of the bearing frame/housing 30 that bisects the bearings 84A-84D. It will also be apparent that the plane defined by the interface between the bearings 84A-84D and the races 88A-88D is likewise perpendicular to the radial line "C" that bisects the bearings 84A-84D. Because of this configuration, load and moment forces in any direction will be transferred radially through the linear bearing assembly 80 to the bearing frame/housing 30.

Although the preferred embodiment has bearings 84A-D on the bogie 52 and races 88A-88D formed in the housing 30, in some instances this arrangement may be reversed. Similarly, though rotating bearing elements have been employed here, some form of anti-friction material that slides or glides along the races could be used instead.

Figure 8:
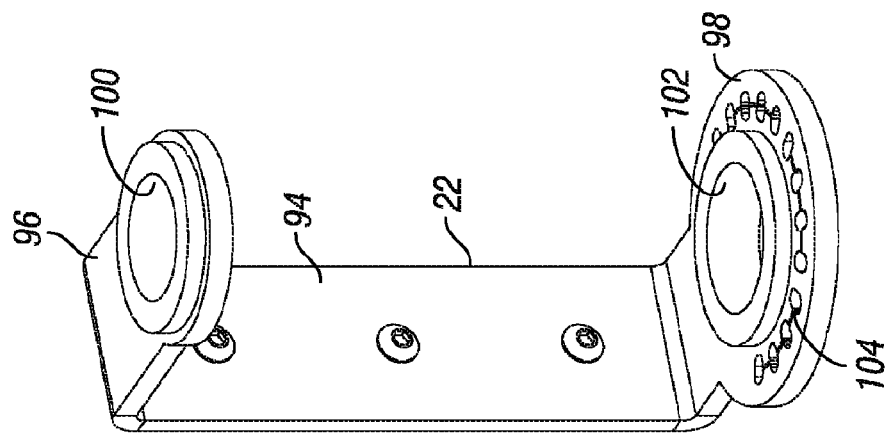
FIG. 8 is a perspective view of the first bracket attachable to the bed frame or other patient transport device.

Turning now to FIG. 8, the preferred configuration for the bracket 22 for attachment to the bed 14 or other patient transport device will be described. The bracket 22 comprises a vertically-oriented, C-shaped brace 94 with horizontally extending upper and lower flanges 96 and 98. Each of the flanges 96 and 98 defines a receptacle for a connector, such as a pin, as will be described hereinafter. Preferably each of the receptacles comprises a bushing 100 and 102, respectively, each with a tapered inner wall. More preferably, each bushing 100 and 102 is formed by a plastic ring that fits into an opening (unnumbered) formed in the flanges 96 and 98; the plastic provides a low friction surface. For reasons that will become apparent as the description continues, the lower flange 98 further comprises a plurality of pin-receiving recesses, such as the holes 104.

The second bracket 24, that is, the bracket that attaches to the tower 20 will be described with reference to FIGS. 9 and 10. Like the bracket 22, the bracket 24 also preferably comprises a vertically-oriented, C-shaped brace 110 with upper and lower horizontally extending flanges 112 and 114. However, instead of bushings, the second bracket 24 is provided with a pair of space-apart, vertically aligned, upwardly pointing conical pins 116 and 118 for a purpose yet to be described. The pins 116 and 118 are attached by bolts 120 and 122. In the most preferred embodiment, the pins are different sizes; for example, the upper pin 116 is larger than the lower pin 118.

Figure 10:
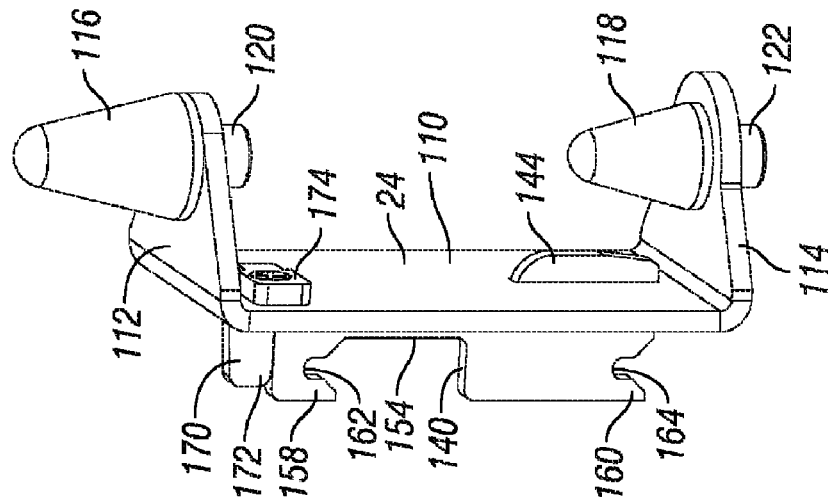
FIG. 10 is an assembled view of the mounting bracket for the tower.
Figure 9:
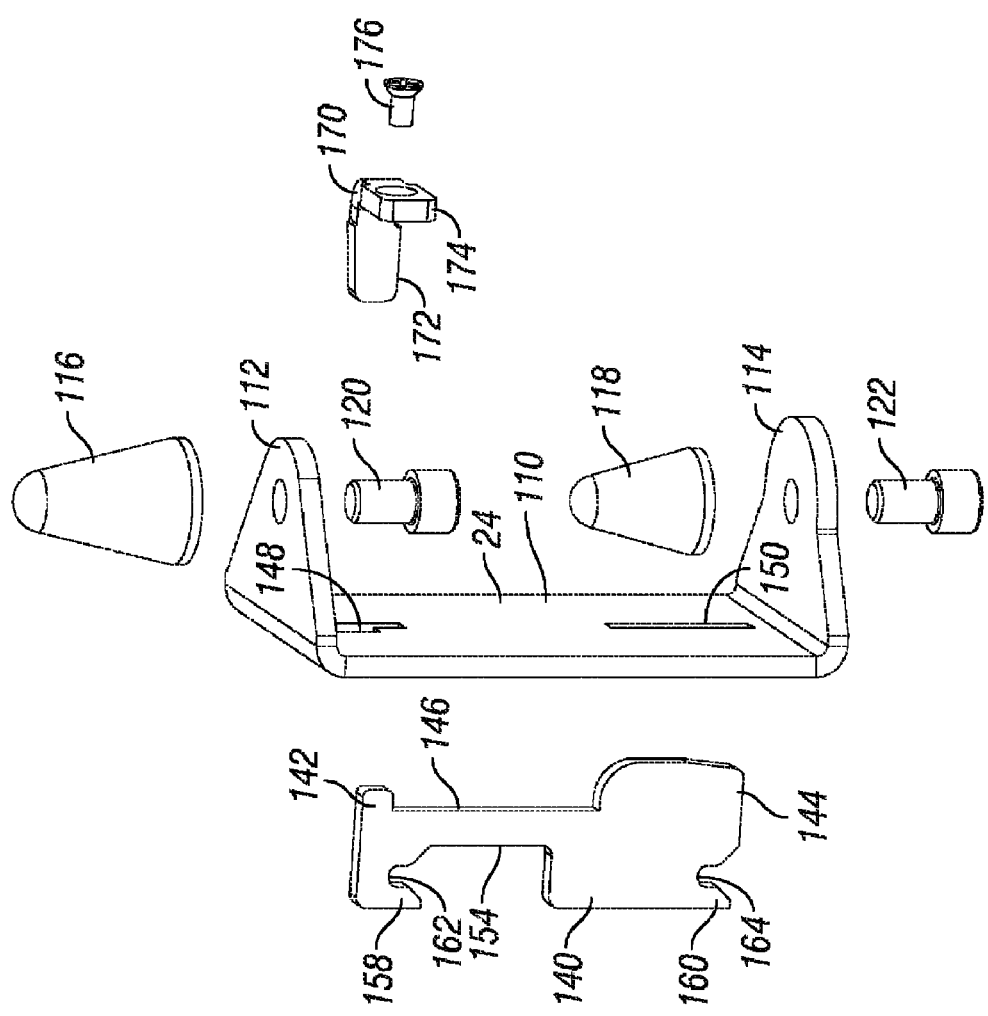
FIG. 9 is an exploded view of the mounting bracket for the tower.

Attachment of the bracket 24 to the bogie 52 is best understood by referring once again to FIGS. 5-7 in conjunction with FIGS. 9 and 10. The bogie 52 includes a fifth spoke 128 that provides a vertical channel or keyway 130. Traversing this keyway 130 are upper, middle and lower rods 132, 134 and 136.

A spline 140 attaches the bracket 24 to the bogie 52. The spline 140 comprises upper and lower inserts 142 and 144 on its outer edge 146 that are receivable in upper and lower slots 148 and 150 in the brace 110. The inner edge 154 of the spline 140 is provided with upper and lower hooks 158 and 160 defining upper and lower notches 162 and 164 sized and positioned to receive the middle and lower rods 134 and 136.

Figure 6:
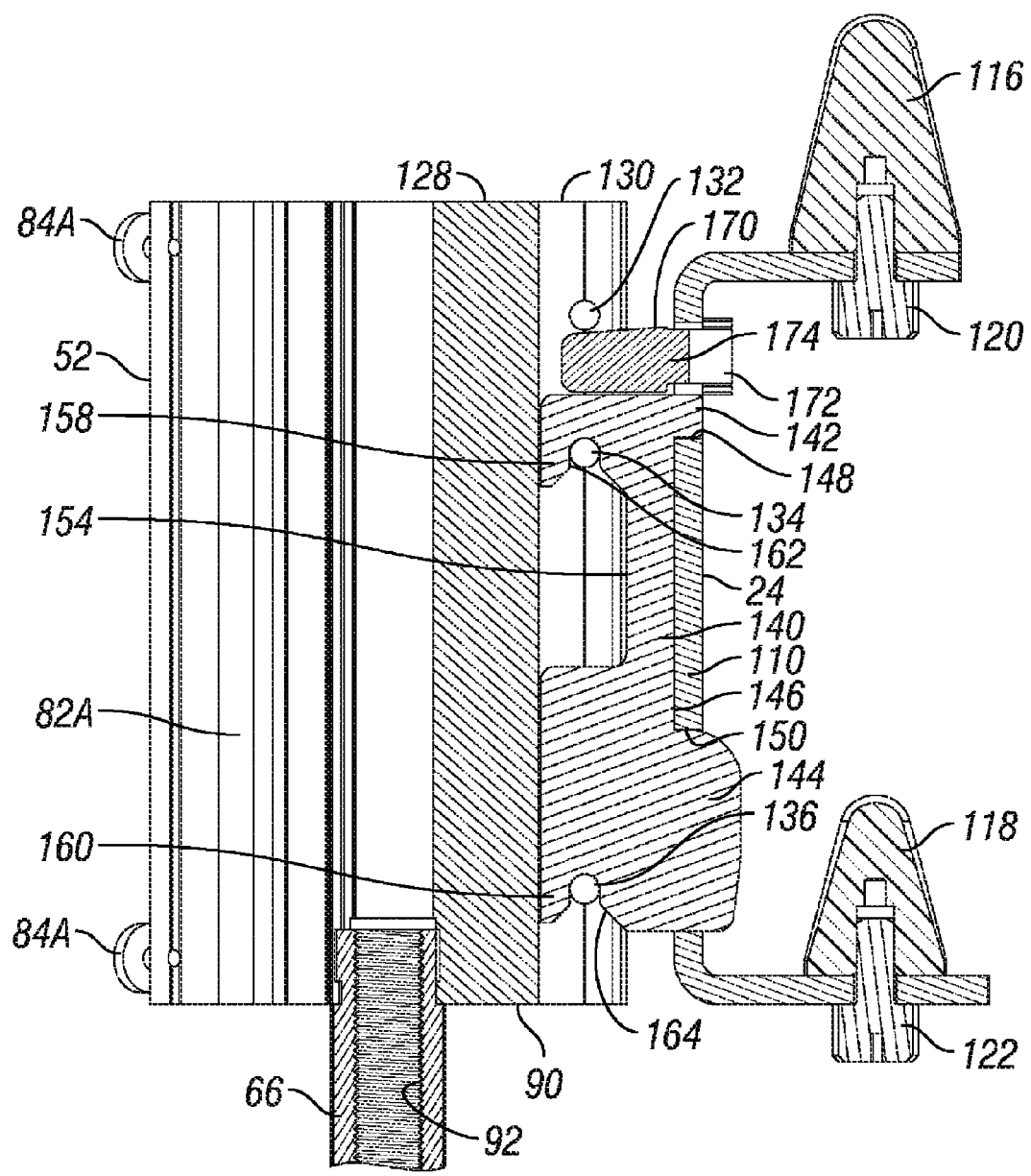
FIG. 6 is a longitudinal sectional view through the bogie with the bracket attached and locked in position.
Figure 7:
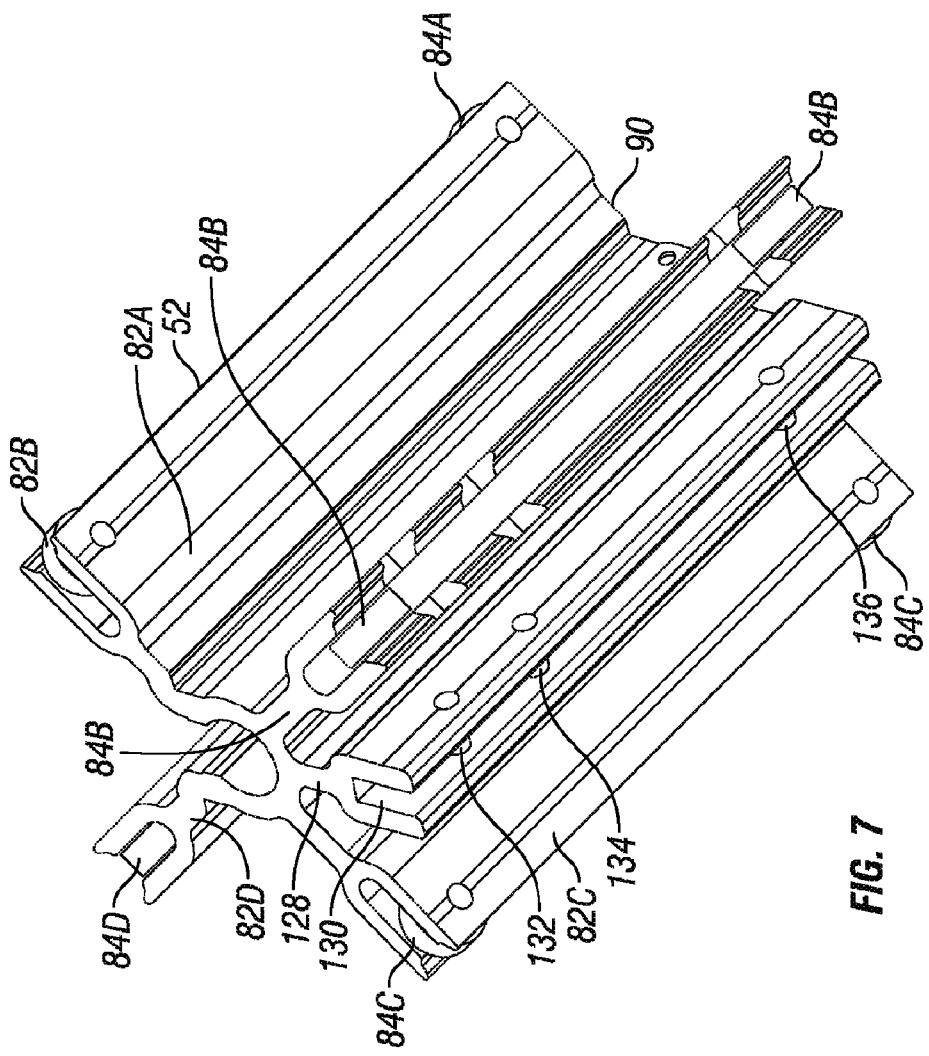
FIG. 7 is a perspective view of the bogie.

With the spline 140 attached to the brace 110, the inner edge 154 of the spline is inserted into the keyway 130 hooking the notches 162 and 164 over the rods 134 and 136 (FIG. 6). Then, the position of the spline 140 in the keyway 130 is secured with a lock bar 170 having a tab 172 that fits through the upper slot 148 in the brace 110 above the insert 142. The tab 172 is long enough to extend through and occupy the space between the upper hook 158 and upper rod 132. In this position, the tab 172 prevents the spline 140 from being withdrawn from the keyway 130. To secure the tab 172 in the locking position, the lock bar 170 has a bolt flange 174 by which the lock bar 170 is bolted to the brace 110 by the bolt 176. In this way, the bracket 24 is removably supported on the bogie 52.

Figure 11:
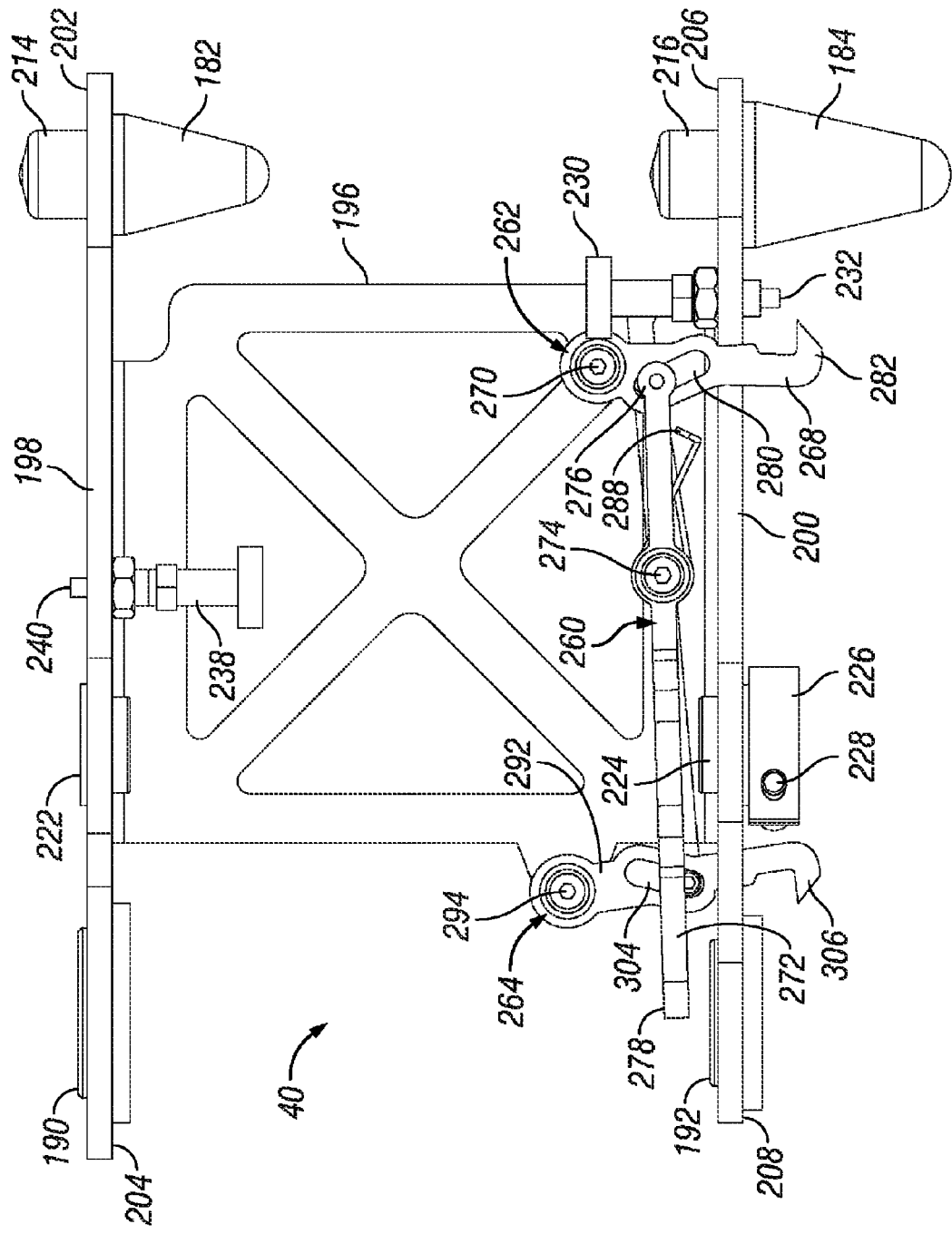
FIG. 11 is a side elevational view of the equipment rack base.
Figure 12:
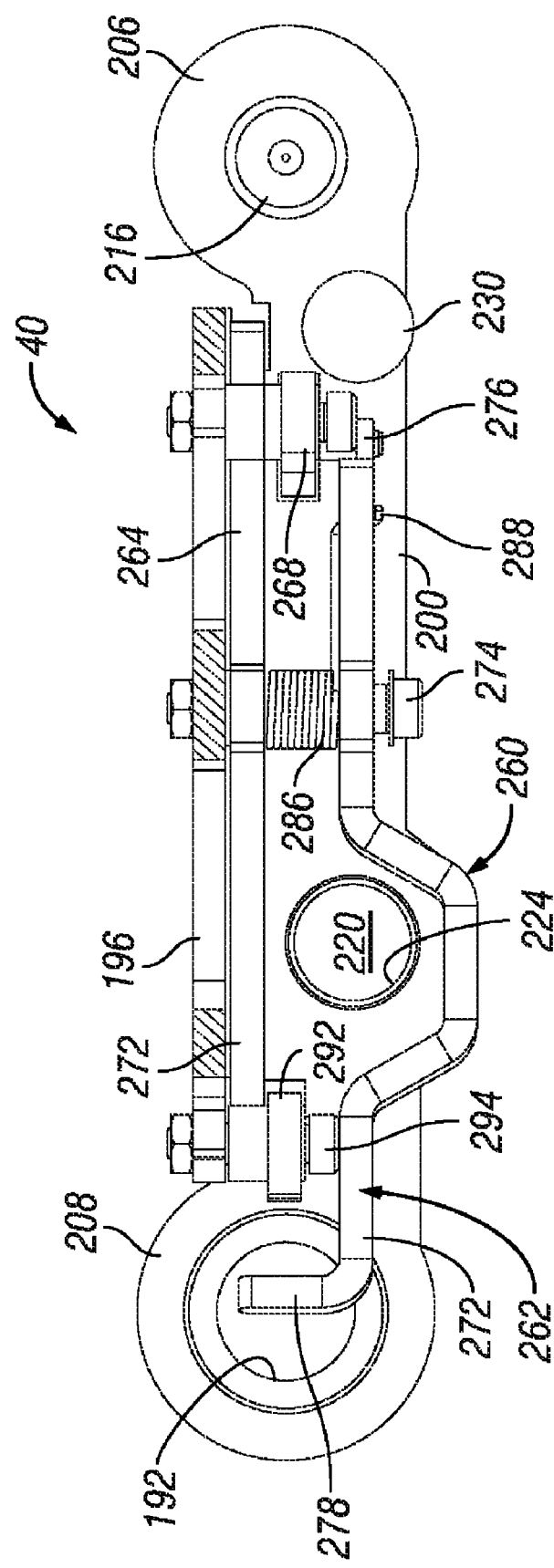
FIG. 12 is a plan view of the rack base.
Figure 13:
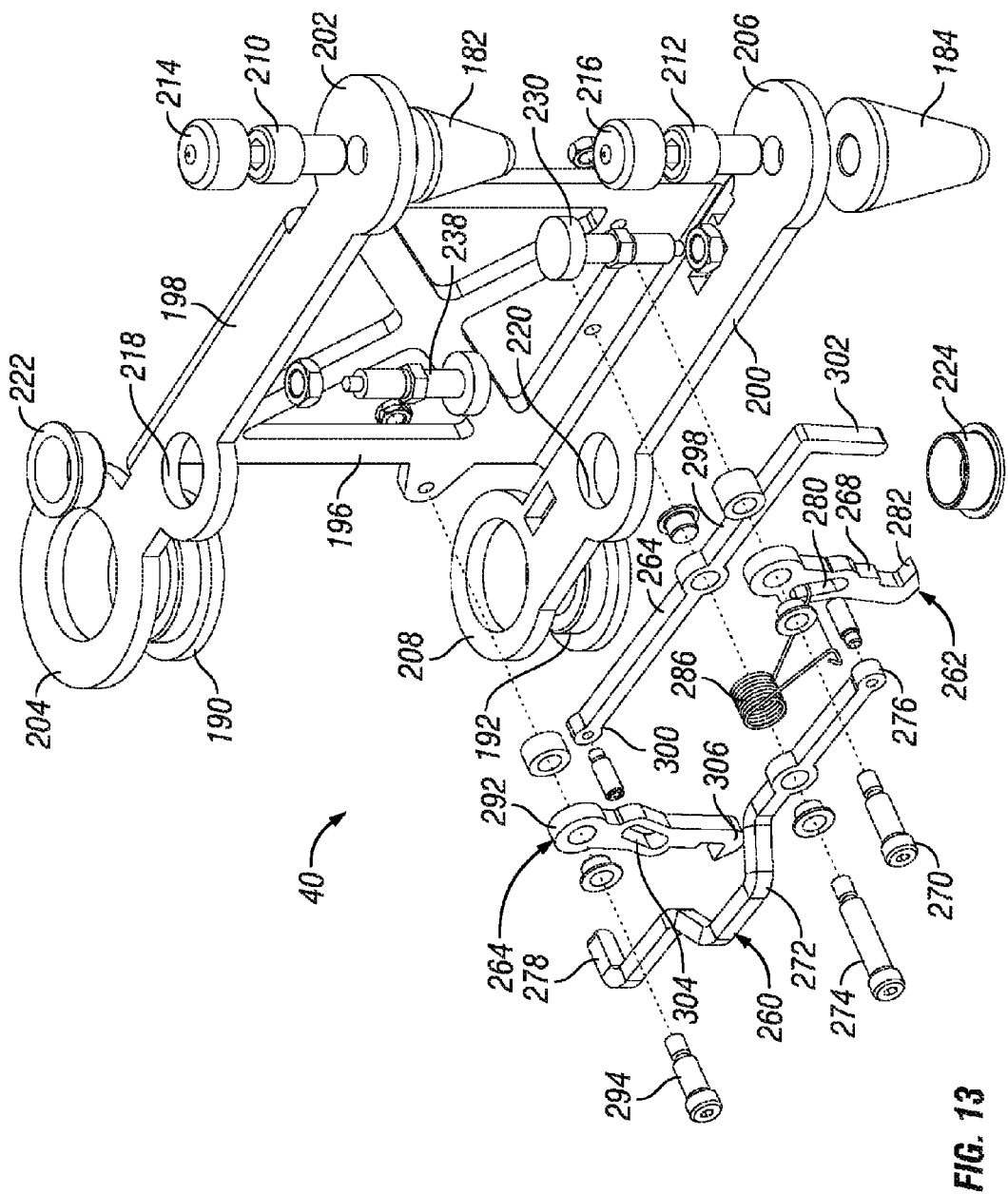
FIG. 13 is an exploded perspective view of the rack base including the latch assembly and the pivot locking pins.

The structure of the preferred rack base 40 is shown in FIGS. 11-13, to which attention is now directed. While the particular configuration of the base 40 may vary, the base preferably provides a support structure for mounting a pair of spaced-apart, vertically-aligned downwardly pointing conical pins 182 and 184 cooperatively sized to be received or nested in the tapered bushings 100 and 102 of the first bracket 22 (FIG. 8). Likewise, the base 40 should provide a mounting for a pair of vertically-aligned tapered bushings 190 and 192 cooperatively shaped to receive the upwardly-extending conical pins 116 and 118 on the second bracket 24 (10).

The rack base 40 may comprise a vertical frame 196 with an upper shelf 198 and a lower shelf 200 extending horizontally from the frame. The upper shelf 198 has a first end 202 for supporting the upper cone 182 and a second end 204 for supporting the upper bushing 100. Similarly, the lower shelf 200 has a first end 206 for supporting the lower pin 184 and second end 208 for supporting the lower bushing 102. The ends 202, 204, 206 and 208 of the shelves 198 and 200 preferably take the form of circular flanges having edges that extend slightly beyond the respective pins and bushings for a purpose that will become apparent. The conical pins 182 and 184 are attached to the first ends 202 and 206, respectively, by bolts 210 and 212. Protective plastic bolt covers 214 and 216 may be applied over the bolt heads to keep dirt and debris from becoming embedded in the bolt head recesses.

As indicated previously, the post assembly 42 (FIG. 3) preferably is removably and pivotally supported on the rack base 40. For this purpose, the upper and lower shelves 198 and 200 are provided with vertically-aligned openings 218 and 220 lined with plastic bushings 222 and 224 to receive the post extension 50. To prevent unintended removal of the post assembly 42 within the rack base 40, the lower bushing 224 may be provided with a split locking ring 226 having a tightening screw 228.

Figure 14:
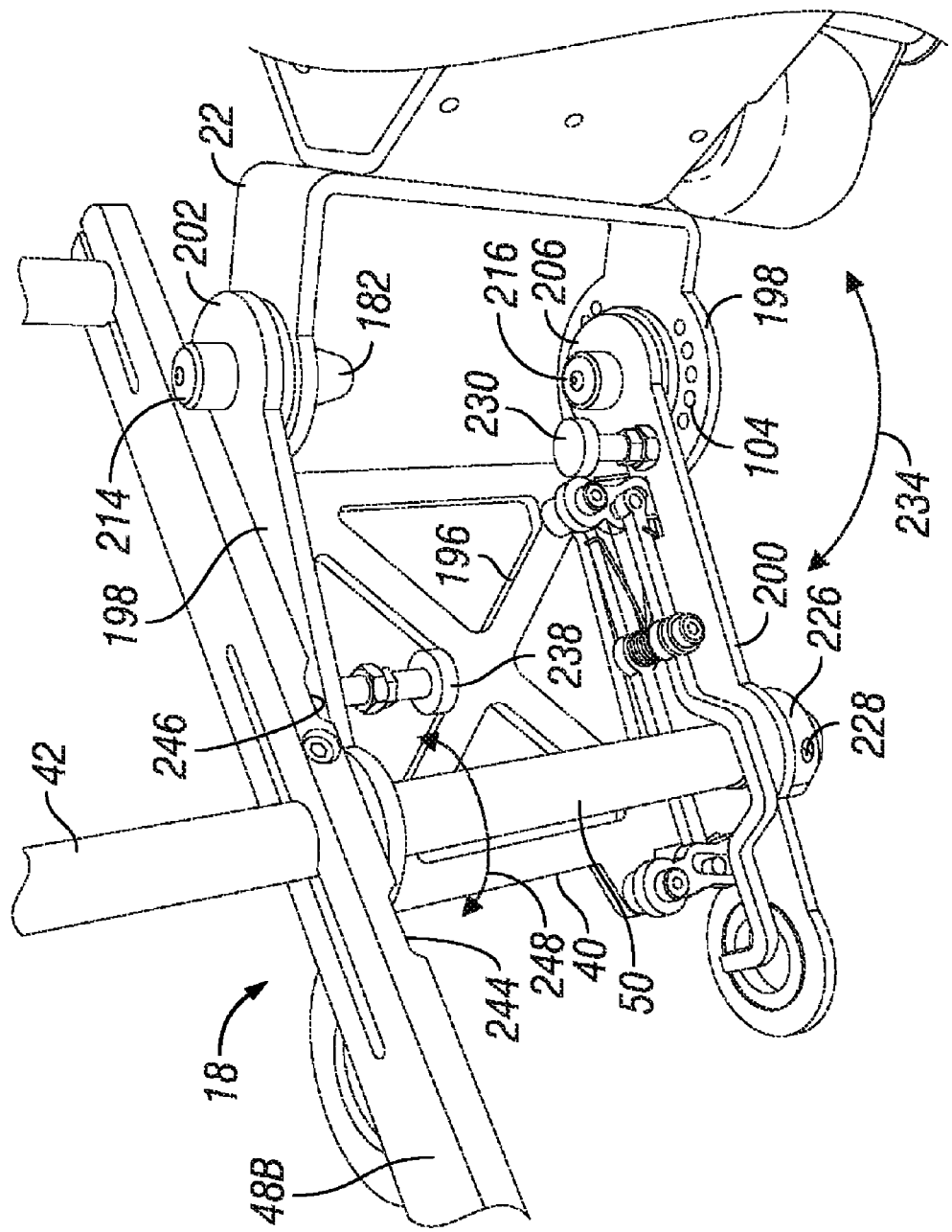
FIG. 14 is a perspective view of the rack base supported on the first bracket on the bed and supporting the post assembly.

As explained above, when the pins 182 and 184 on the rack 18 are nested in the bushings 100 and 102 of the first bracket 22 so that the rack is supported on the bracket, the pin-bushing joint permits rotation of the rack relative to the bracket to one of a plurality of selected positions. This feature of the system 10 is depicted in FIG. 14. The possible positions correspond to the holes 104 in the lower flange 102 of the first bracket 22 (FIG. 8). The selected position is secured by means of a first retractable pivot control pin 230 mounted on first end 206 of the bottom shelf 200 of the frame 196. The pin end 232 (FIGS. 11, 13) extends downwardly so that when it is retracted, the rack 18 is movable relative to the first bracket 22 and so that when it is extended it engages one of the holes 104 to retain the rack base in the selected one of the plurality of position. Thus, the rack base 42 is pivotally movable on the bracket 22 in the direction indicated by the line 234 (FIG. 14) in an arc of about 270 degrees. The pin 230 preferably is biased, as by a spring, in the extended position.

With continuing reference to FIG. 14, and also to FIGS. 11-13, a second pivot control pin 238 is included on the upper shelf 198 of the rack base 40 to lock the post assembly in a selected position relative to the rack base. The second pin 238 extends upwardly to engage one of two recesses (not shown) on the underside of the lower horizontal bar 48B of the post assembly 42. The pin end 240 access the recesses by chamfered notches 244 and 246 formed in the edge of the bar 48B. The pin 238 preferably is biased, as by a spring, in the extended position. Thus the post assembly 42 rotates along the line indicated at 248 and can be retained by the extended pin 238 in a plurality of positions, such as the first position, seen in FIG. 14, and a second position rotated to the right in FIG. 14 so that the pin moves through the notch 238.

Referring still to FIGS. 11-13, the preferred latch assembly is also illustrated and referred to herein generally by reference numeral 260. The latch assembly 260 is adapted to secure the rack 18 alternately to the first and second brackets 22 and 24 as the rack is transferred between the bed 14 (or other patient transport device) and the tower 20. Most desirably, the latch assembly 260 is both self-locking and self-releasing. In other words, the latch assembly 260 is configured to lock and release the rack 18 automatically as the rack is moved between the bed bracket 22 and the tower bracket 24, without additional actions of the user.

The exemplary latch assembly 260 comprises a first latch 262 engagable with the first bracket 22 and a second latch 264 engagable with the second bracket 24. Preferably, the first and second latches 262 and 264 are independently operable.

The first latch 262 comprises a first cam 268 pivotally mounted to the frame 196 at 270 for movement between closed position and an open position, to be explained hereafter. The first latch 262 also includes a first lever 272 for operating the first cam 268. The first lever is pivotally mounted at 274 on the frame 196. The first end 276 of the lever 272 operatively connects to the first cam 268 to control its movement, and the second end forms a foot 278. The first end 276 moves from end to end in the slot 280 in the first cam 268 as it pivots, thus moving the hook 282 on the free end of the first cam between the open and closed positions. The first lever 272 thus is mounted for movement between an engaged position and a disengaged position, to be explained below.

The first lever 272 preferably is biased toward the engaged position. For this purpose, a coil spring 286 is employed. One end 288 of the spring 286 impinges on the underside of the first lever 272 near the first end 276 urging it upwards in the slot 280 in turn urging the hook 282 of the first cam 268 into the closed position.

Still referring to FIGS. 11-13, the second latch 264 comprises a second cam 292 pivotally mounted to the frame 196 at 294 for movement between closed position and an open position, to be explained hereafter. The second latch 264 also comprises a second lever 298 having a first end 300 operatively connected to the second cam 292 to control its movement. The second end of the second lever 298 forms a foot 302. The first end 300 moves from end to end in the slot 304 in the second cam 292 as it pivots, thus moving the hook 306 on the free end of the second cam between the open and closed positions. The second lever 298 thus is mounted for movement between an engaged position and a disengaged position, also to be explained below.

The second lever 298 preferably is biased toward the engaged position, preferably by the second end 306 of the coil spring 286 which is hooked over the top of the second end 302 of the second lever 298. As the end 306 of the spring 286 presses down on the second end 302 of the second lever 298, the first end 300 is urged upward in the slot 304 in turn urging the hook 306 on the end of the second cam 292 into the closed position.

Figure 15A:
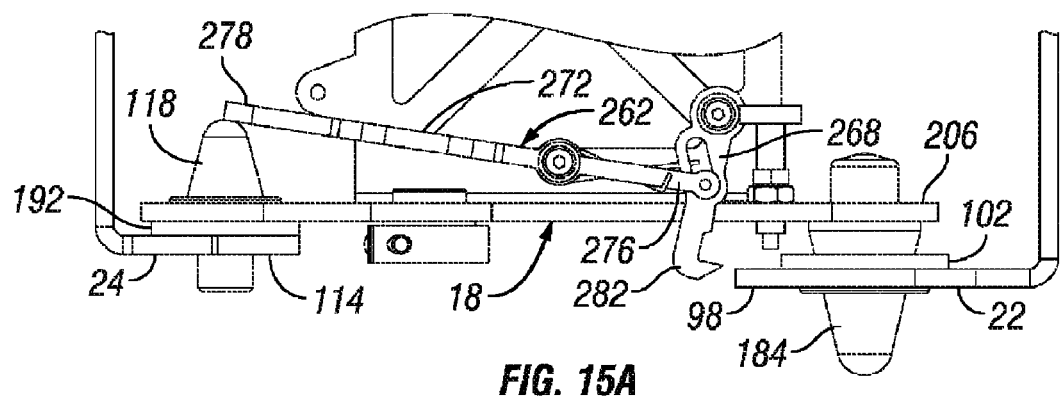
FIGS. 15A-C illustrate the operation of the first latch lever and cam that engage the bracket on the bed.

The operation of the latches 262 and 264 will be explained with the aide of FIGS. 15 and 16. FIGS. 15A-15C show only the first latch 262. In FIG. 15A, the rack 18 is supported entirely on the second bracket 24. Only the lower flange 114 with the lower pin 118 of the bracket 24 is shown to simplify the illustration. The cone 118 is fully inserted in the bushing. The foot 278 of the first lever 272 is positioned over pin 118 so that as the tip of the pin goes up and down in the bushing 192 the foot likewise rises and falls and thereby causes simultaneous and opposite movement of the first end 276 of the first lever. Thus, in FIG. 15A, where the foot 278 is pushed to its uppermost position by the pin 118, the first cam 268 is pulled to its open position retracting the hook 282 away from the flange 98.

Figure 15B:
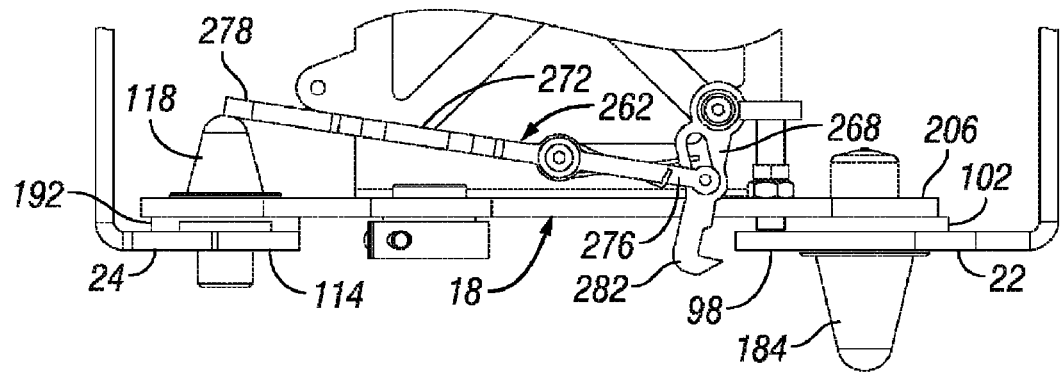
Figure 15C:
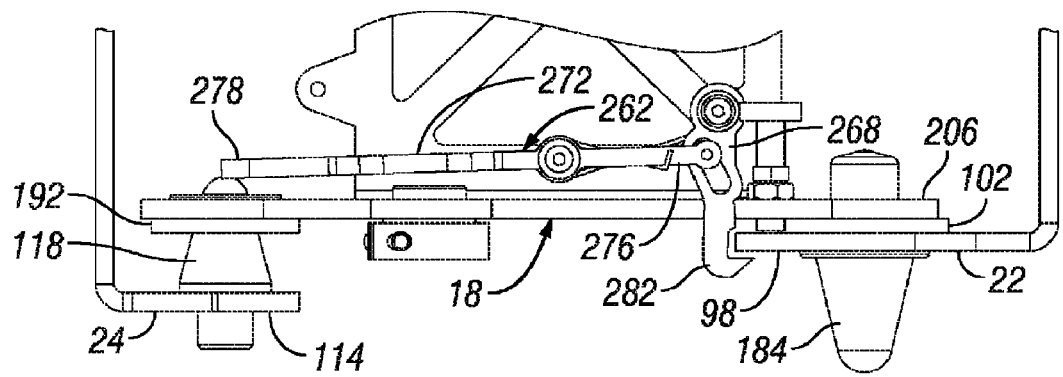

Again, only the lower flange 98 and lower bushing 102 of the bracket 22 is shown in FIGS. 15A-15C. In this open, disengaged position the rack 18 may be raised and lowered by the tower 20 positioning the pin 184 down into the bushing 102. In FIG. 15A, the pin 184 is being lowered into the bushing 102 on the flange 98 of the first bracket 22.

As shown in FIG. 15B, the rack 18 is lowered until the flange 206 abuts the bushing 102 and the pin 184 is fully seated therein. At this point, the weight of the rack 18 is shared between the first and second brackets, 22 and 24, or more accurately, between the bed 14 and the tower 20.

As the lift mechanism in the tower 20 continues to lower the rack 18, the pin 118 on the second bracket 24 begins to recede or withdraw from the bushing 192 on the flange 114. As seen in FIG. 15C, as the pin 118 recedes the foot 278 lowers, being urged downwardly by the spring 286 (FIGS. 12 & 14). Simultaneous, the cam 268 pivots to its closed position so that the hook 282 entraps the flange 98 around the cone 184. This locks the rack 18 to the first bracket 22.

Figure 16A:
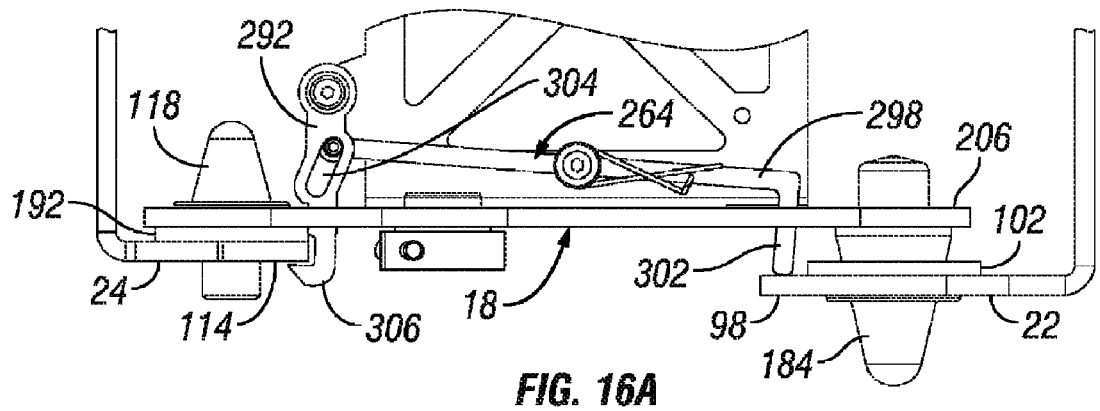
FIGS. 16A-C illustrate the operation of the second latch lever and cam that engage the bracket on the tower.

Moving to FIGS. 16A-16C, the operation or the second latch 264 will be described. Again, starting with the rack 18 fully supported on the second bracket 24 (on the tower 20), the spring is urging the foot 302 on the second end of the lever 298 into the downward or resting position. This pushes the second cam 292 into the closed position with the hook 306 gripping the flange 114 on the bracket 24. This locks the rack 18 to the second bracket 24 on the tower 20. Using the lift mechanism in the tower, the rack 18 is positioned so that the pin 184 is positioned over the bushing 102.

Figure 16B:
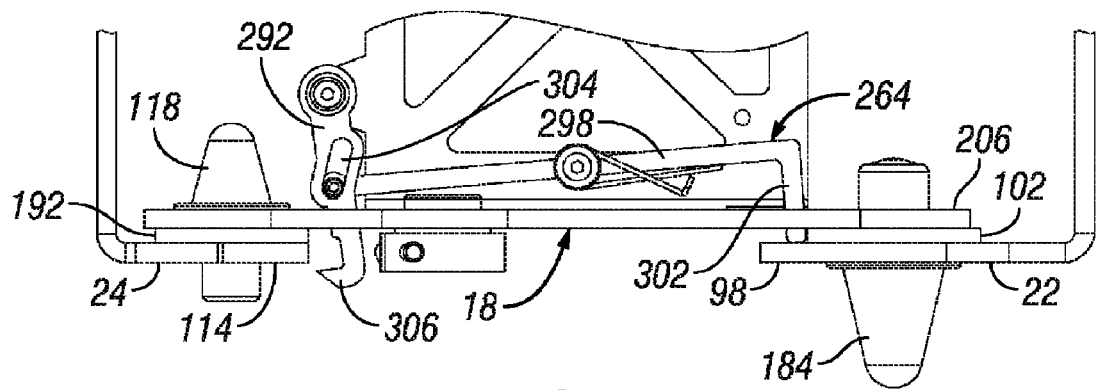

As seen in FIG. 16B, as the rack is lowered, the pin 184 is lowered into the bushing 102 in the first bracket 22 until the weight of the rack 18 is shared between the brackets 22 and 24 equally. As this occurs, the flange 98 impinges on the foot 302 of the lever 298, thus moving the lever into the disengaged position and the second cam 292 into the open position. This releases the grip of the hook 306 from the flange 114

Figure 16C:
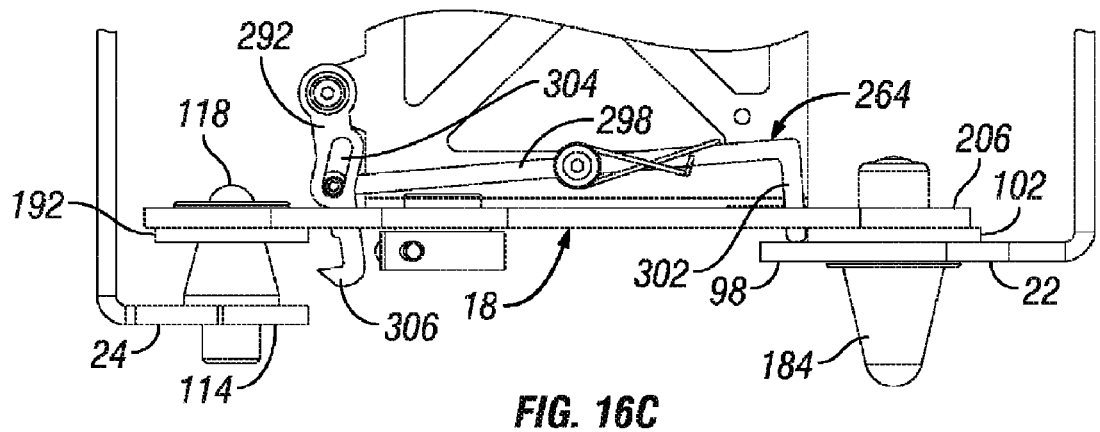

As seen in FIG. 16C, as the tower continues to lower the second bracket 24, the pin 118 is withdrawn from the flange 114 leaving the rack 18 supported entirely on the first bracket 22.

Figure 17:
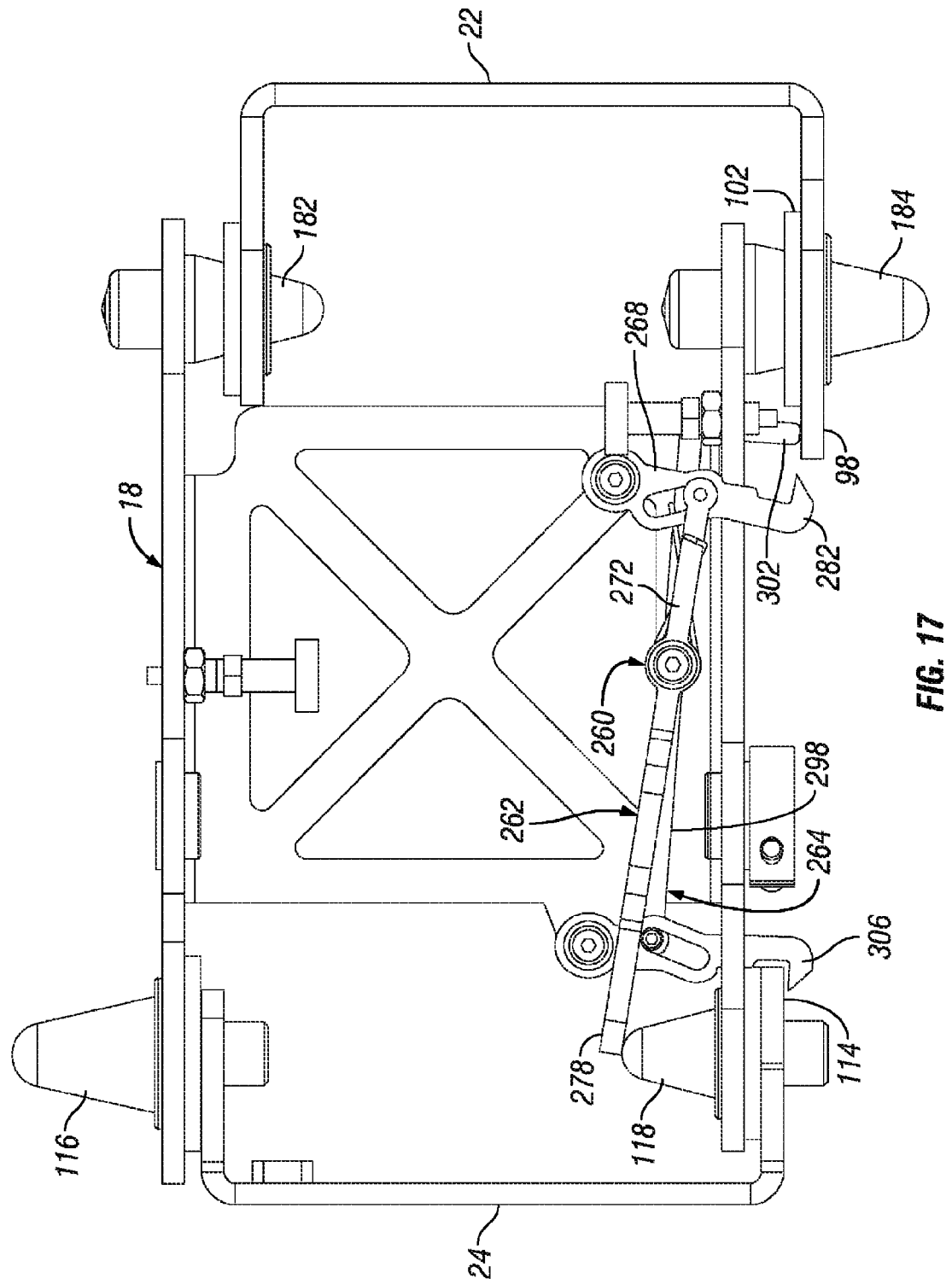
FIGS. 17-19 illustrate the simultaneous operation of the first and second latch latches as the equipment rack is transferred from the tower to the bed.
Figure 18:
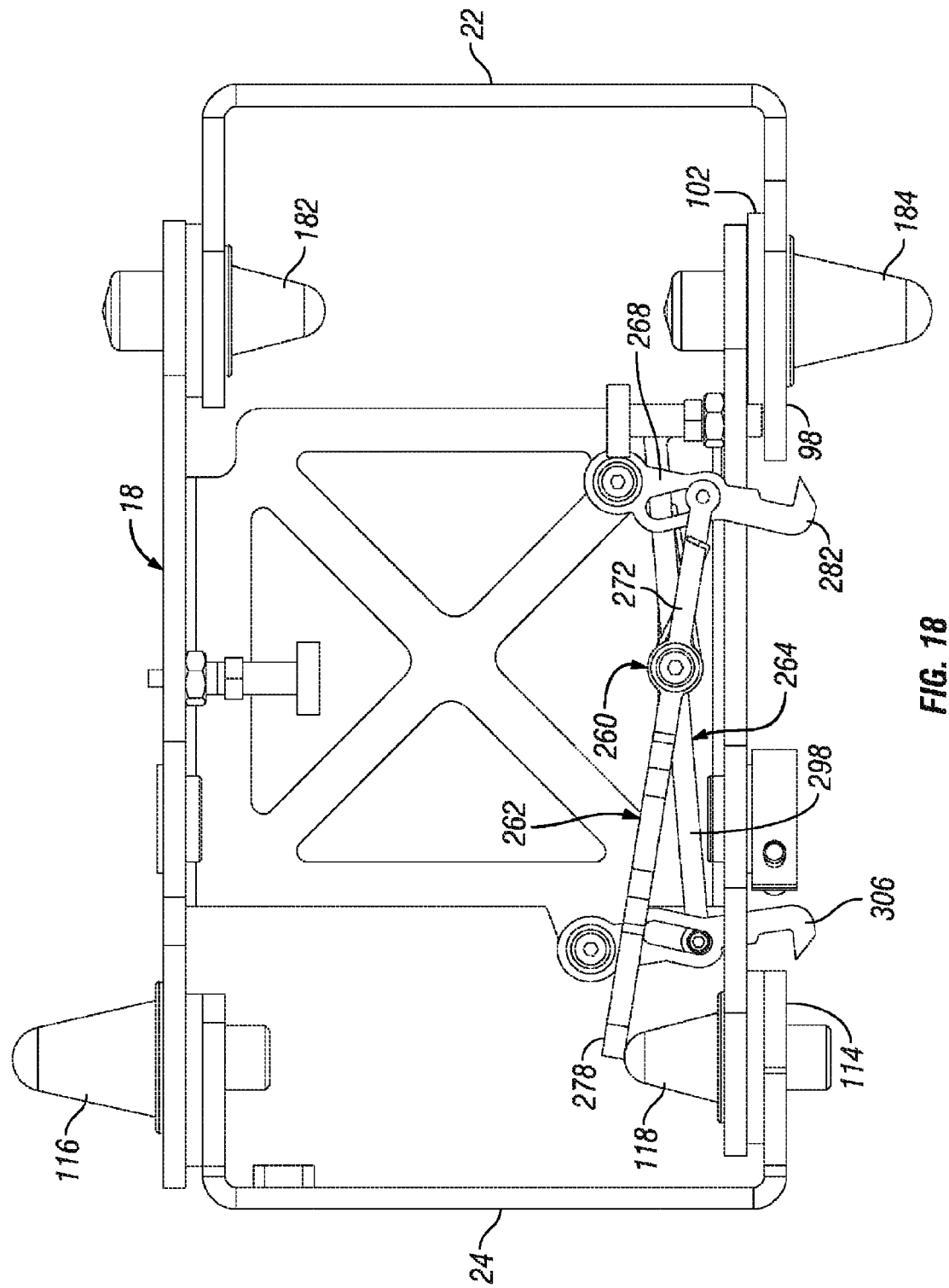
Figure 19:
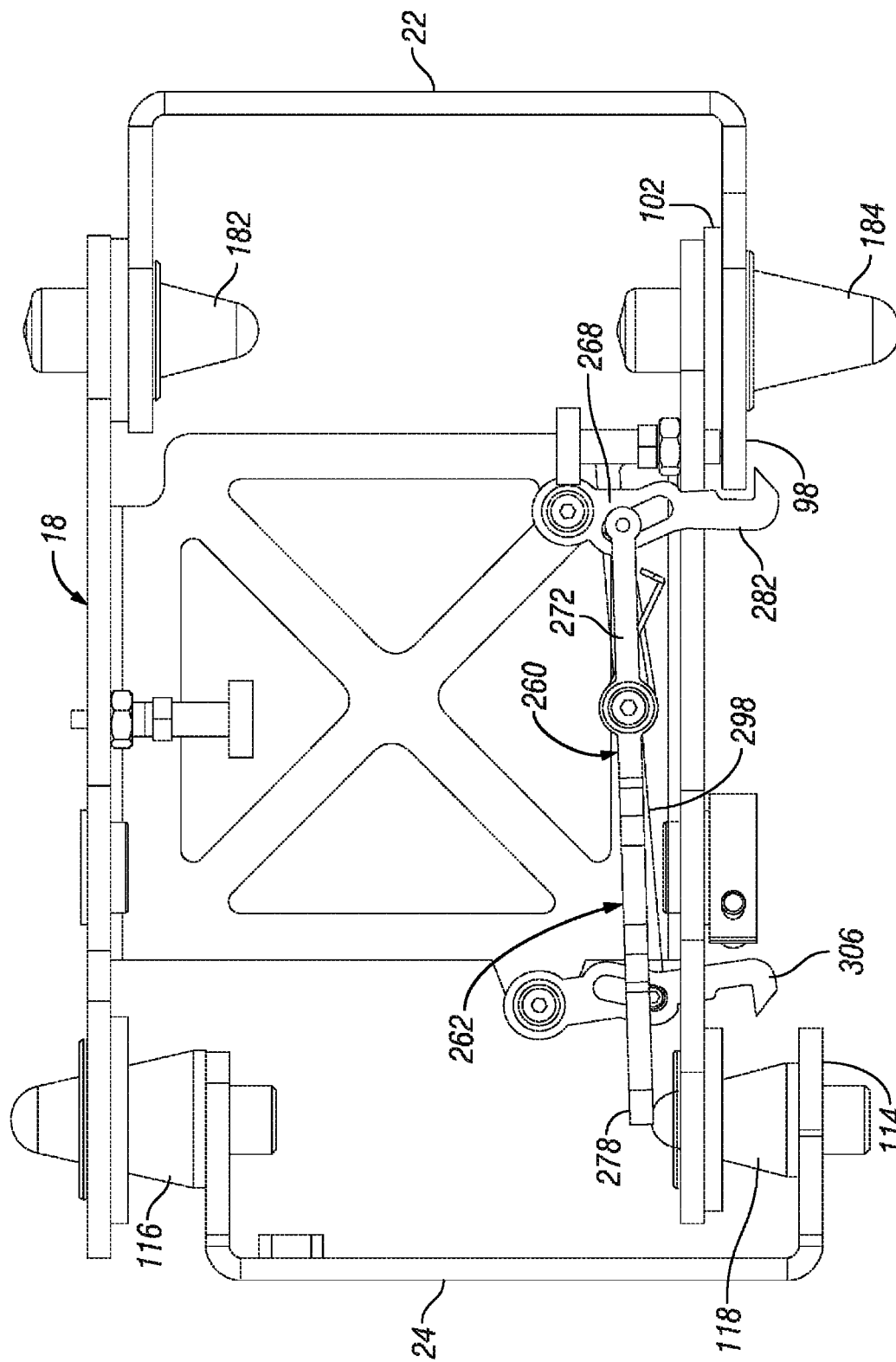

FIGS. 17-19, to which we now turn, illustrate the simultaneous action of the first and second latches 262 and 264. FIG. 17 corresponds to FIGS. 15A and 16A and shows the rack 18 supported entirely on the second bracket 24, similar to the position seen in FIG. 1. The first latch 262 is open or disengaged because the pin 118 is holding the foot 278 in the upward most position, retracting the hook 282 from the flange 98 on the first bracket 22. The second latch 264 is engaged because the flange 102 has not yet risen high enough to displace the foot 302.

FIG. 18 corresponds to FIGS. 15B and 16B, in which the weight of the rack 18 is shared equally between the brackets 22 and 24. The rack 18 has been lowered until the foot 302 (FIG. 17) was forced upward, thus retracting the hook 306 from the flange 114 on the second bracket, so that both the latches 262 and 264 are disengaged, that is, both hooks 282 and 306 are open. This permits withdrawal of the rack 18 from the first bracket 22.

FIG. 19 corresponds to 15C and 16C and shows the rack 18 now transferred to the first bracket 22, similar to the position in FIG. 2. The receding pin 118 on the second bracket 24 has allowed the foot 278 of the first latch 262 to return to the resting or engaged position, moving the hook 282 into the closed position with the flange 98 on the first bracket 22. Now, the tower 20 (not seen in FIG. 19) with the second bracket 24 attached may be rolled away from the bed 14 (FIG. 2) freeing the patient for transport with the rack 18 supported on and locked to the bracket 22.

Now it will be appreciated that as the rack 18 is lowered, the first latch 262 is automatically engaged and the second latch 264 is automatically, independently and simultaneously disengaged. No separate or additional action by the using is necessary. All the user is required to do is operate the switch 72 (FIG. 4) to raise or lower the lift mechanism and position the pins 114 and 116, or 182 and 184, for transfer. As the weight of the rack 18 is shifted from one bracket to the other, the latch assembly 260 automatically locks the rack 18 to the bracket to which it is being transferred and automatically releases the rack 18 from the bracket from which it is being transferred.

Regarding the alignment and positioning of the pins 114 and 116, or 182 and 184, it will now be understood that the conical shape self-centers the pins as they approach the respective bushings 100 and 102, and 190 and 192. In addition, as is seen in FIGS. 17-19, the upper pin 182 is smaller than the lower pin 184 on the first bracket 22, and the lower pin 118 is smaller than the upper pin 116 on the second bracket 24. This size difference prevents operation of the latch assembly 260 unless both of the pins in a pair are properly position. The latch will not release one bracket until the other rack 18 is properly supported on flanges of the other bracket.

Figure 20:
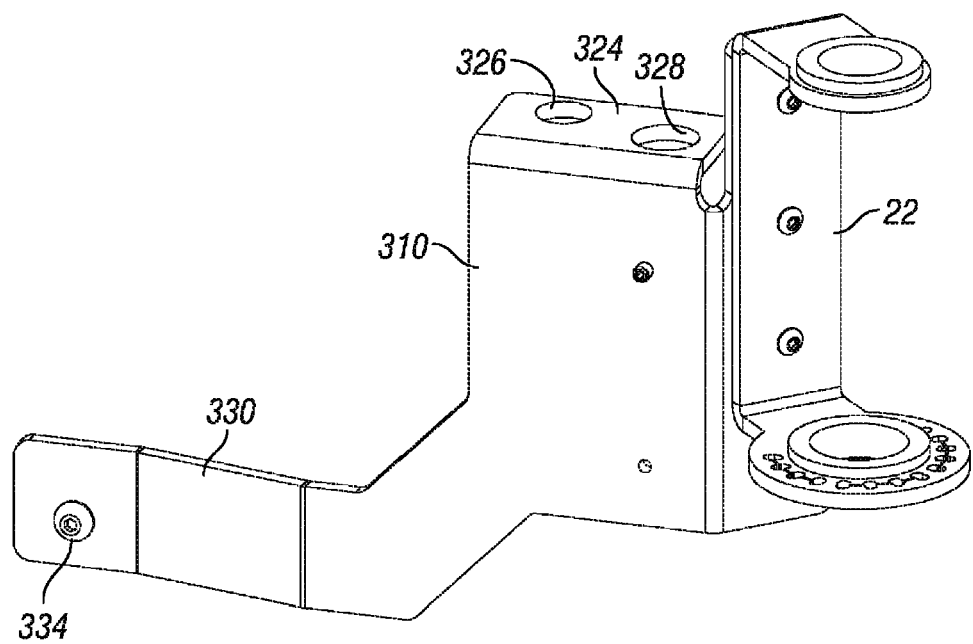
FIG. 20 is a frontal perspective view of the bed bracket attached to an adapter for mounting the bracket to the bed.
Figure 21:
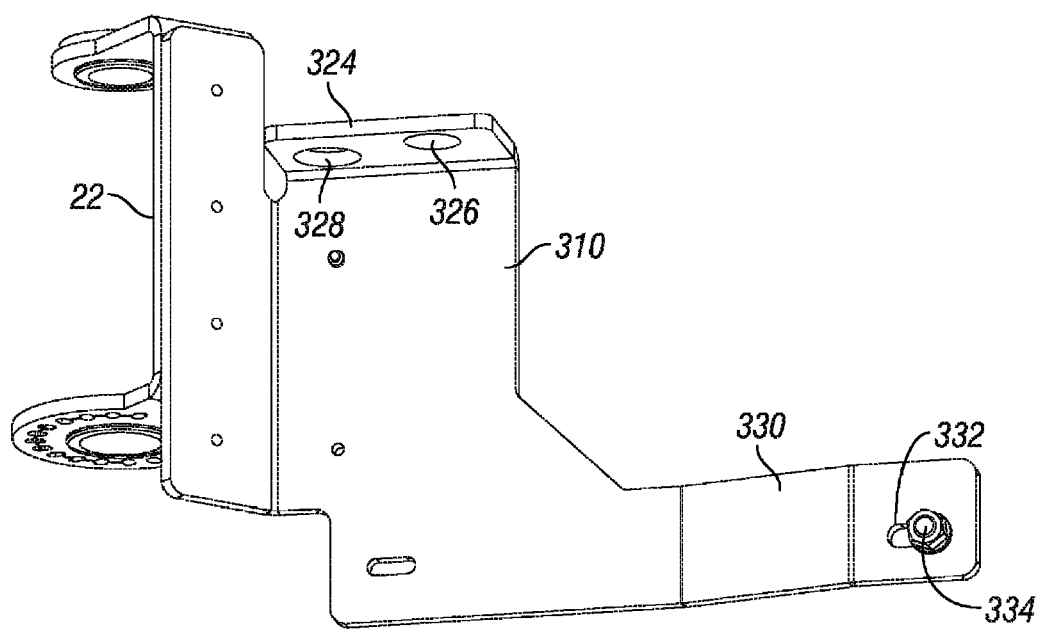
FIG. 21 is a rear perspective view of the bed bracket and adapter.
Figure 22:
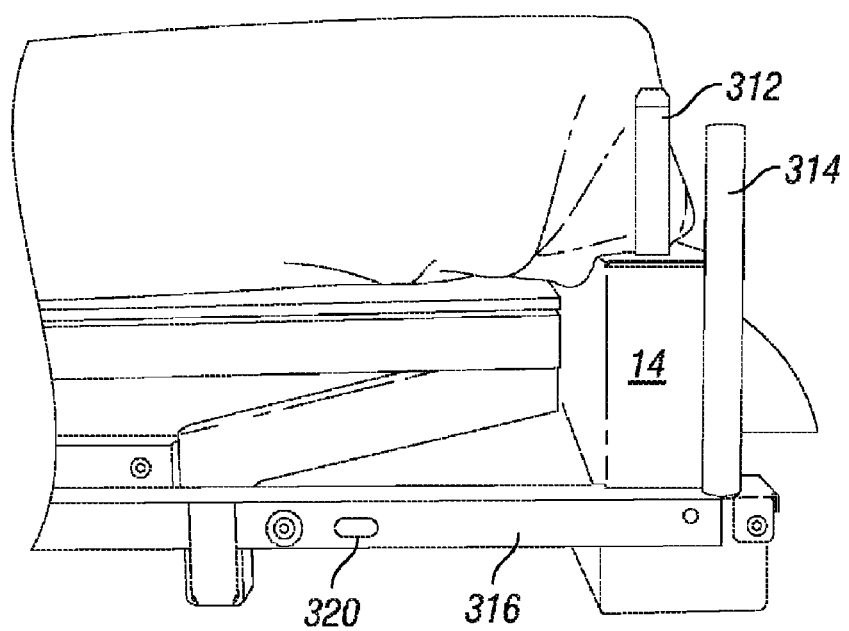
FIG. 22 is a side view of a bed showing the corner structure to which the adapter is mounted.
Figure 23:
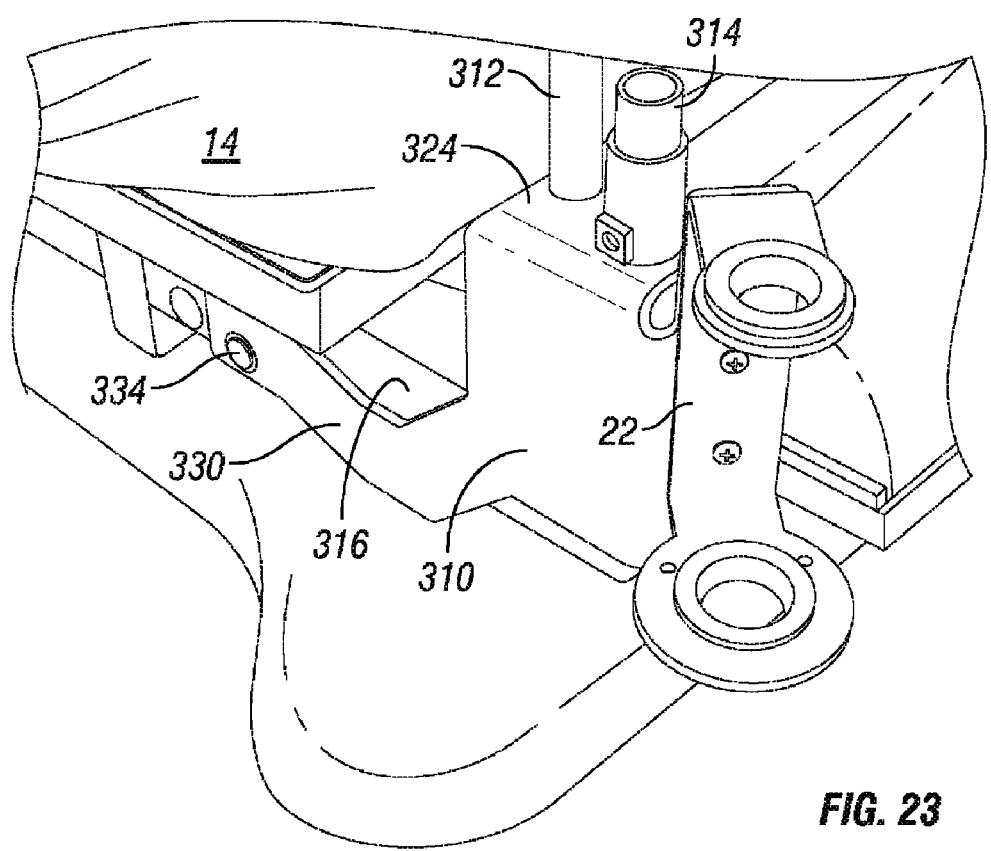
FIG. 23 is a perspective view of the bed bracket and adapter mounted to the bed shown in FIG. 22.

Yet another advantageous feature of the system 10 of the present invention will be described with reference to FIGS. 20-23. FIG. 20 shows the first bracket 22 bolted to an adapter 310. FIG. 22 shows the corner of the frame of the bed 14 (FIGS. 1 & 2) before attachment of the bracket 22, and FIG. 23 shows the adapter 310 bolted to the bed 14. The particular bed illustrated in these figures is a Stryker Epic II model. This model bed has vertical tubular members 312 and 314 for supporting IV poles, and the horizontal rail 316 includes slots 320. The adapter 310 is customized to fit on the bed 14 without making any additional holes in the frame or welding any additional structures to it. Thus, this adapter 310 has a horizontal flange 324 with two holes 326 and 328 sized and positioned to receive the tubular members 312 and 314, as seen best in FIG. 23. The adapter 310 also comprises a elongate arm portion 330 with a bolt hole 332 so that a bolt 334 may be used to attach the arm portion.

Adapters customized for the customer's bed model may be included with the system 10. This makes installation simple, and eliminates the need to modify the bed frame to attach the bracket 22, which might void the warranty on the bed.

The embodiments shown and described herein are exemplary. Some elements or features of the present invention may be found in the art and, therefore, have not been described in detail herein. The description and drawings are illustrative only, and changes may be made in the combination and arrangement of the various parts and elements described herein without departing from the spirit and scope of the invention as defined in the following claims. The description and drawings do not point out what an infringement of this patent would be, but rather merely provide one example of how to use and make the invention. The limits of the invention and the bounds of the patent protection are measured by the claims.

What is claimed is:

1. A medical equipment transport system for supporting medical equipment near a patient being transported on a patient transport device, the system comprising:
    a tower comprising:
        a bearing frame having a central longitudinal axis;
        a bogie supported for vertical movement inside the frame along the central longitudinal axis;
        a bearing assembly between the bearing frame and the bogie comprising:
            at least three bearings positioned radially equidistantly around the central longitudinal axis;
            at least three vertically-oriented, linear bearing races disposed equidistantly about the central longitudinal axis of the bearing housing;
            wherein the at least three bearings are supported on the bogie, one bearing supported for movement along each of the races as the bogie moves vertically in the bearing frame;
            so that load and moment in any direction on the bogie will be transferred radially through the bearing assembly to the bearing frame and
        a drive assembly for driving the vertical movement of the bogie;
    a first bracket attachable to the patient transport device;
    a second bracket supportable on the bogie for movement therewith; and
    a medical equipment rack removably supportable on the first and second brackets.

2. The medical equipment transport system of claim 1 wherein the bearings are roller bearings rotatably supported on the bogie.

3. The medical equipment transport system of claim 2 wherein the bearings are cylindrical roller bearings, each having an axis of rotation.

4. The medical equipment transport system of claim 3 wherein the bogie comprises at least three radially-extending spokes, each spoke supporting one of the at least three bearings in one of the races, wherein the rotational axis of each of the at least three bearings is perpendicular to a line extending radially from the central longitudinal axis of the bearing frame and bisecting the bearing.

5. The medical equipment transport system of claim 4 wherein the at least three spokes comprises four spokes, wherein the at least three bearings comprises four bearings, and wherein the at least three races comprises four races.

6. The medical equipment transport system of claim 5 wherein the bogie is vertically elongated and wherein the at least three bearings comprises two bearings vertically aligned on each spoke.

7. The medical equipment transport system of claim 1 wherein the drive assembly is characterized as converting rotary motion to linear motion.

8. The medical equipment transport system of claim 7 wherein the drive assembly comprises a screw drive.

9. The medical equipment transport system of claim 8 wherein the drive assembly comprises a ball screw.

10. The medical equipment transport system of claim 9 wherein the rotation is motorized.

11. The medical equipment transport system of claim 1 wherein the drive assembly is motorized.

12. The medical equipment transport system of claim 1 wherein the second bracket comprises a pair of spaced apart, vertically-aligned, upwardly-pointing conical pins, wherein the rack comprises a pair of cooperatively configured tapered bushings to receive the pins on the second frame support bracket, wherein the rack comprises a pair of spaced apart, vertically-aligned, downwardly-pointing conical pins, and wherein the first bracket comprises a pair of cooperatively configured tapered bushings to receive the pins on the rack.

13. The medical equipment transport system of claim 12 where in each of the pairs of cones, one cone is larger than the other.

14. The medical equipment transport system of claim 12 comprising a self-locking and self-releasing latch assembly adapted to secure the rack alternately to the first and second brackets as the rack is transferred between the patient transport device and the tower.

15. The medical equipment transport system of claim 14 wherein the latch assembly comprises a first latch engagable with the first bracket and a second latch engagable with the second bracket.

16. The medical equipment transport system of claim 15 wherein the first and second latches are independently operable.

17. The medical equipment transport system of claim 16 wherein the first latch comprises:
    a first cam pivotally mounted to the rack for movement between a closed position and an open position, wherein in the closed position the first cam locks the first bracket to the rack, and wherein in the open position, the first cam is disengaged from the first bracket; and
    a first lever for operating the first cam, the first lever being pivotally mounted to the rack for movement between an engaged position, in which the first cam is closed, and a disengaged position, in which the first cam is open, wherein the first lever is biased towards the engaged position, and wherein the first lever has a first end operatively connected to the first cam to control movement thereof, and a second end engagable with the second bracket so that when the rack is disengaged from the second bracket the first lever is in the engaged position and the first cam is closed thereby locking the rack to the first bracket, and so that when the rack is supported on the second bracket the first lever is in the disengaged position and the first cam is open thereby releasing the rack from the first bracket.

18. The medical equipment transport system of claim 17 wherein the first bracket comprises a flange extending from one of the tapered bushings and the first cam comprises a hook configured to receive the flange to lock the rack to the first bracket, wherein first lever comprises a foot positioned to engage one of the conical pins on the second bracket so that when the pin is fully seated in the bushing, the first lever is pushed toward the disengaged position releasing the first bracket and when the pin is withdrawn from the bushing, the first lever returns to the engaged position locking the rack to the first bracket.

19. The medical equipment transport system of claim 18 wherein the second latch comprises:
   a second cam pivotally mounted to the rack for movement between closed position and an open position, wherein in the closed position the second cam locks the second bracket to the rack, and wherein in the open position, the second cam is disengaged from the second bracket; and
   a second lever for operating the second cam, the second lever being pivotally mounted to the rack for movement between an engaged position, in which the second cam is closed, and a disengaged position, in which the second cam is open, wherein the second lever is biased towards the engaged position, and wherein the second lever has a first end operatively connected to the second cam to control movement thereof, and a second end engagable with the first bracket so that when the rack is disengaged from the first bracket the second lever is in the engaged position and the second cam is closed thereby locking the rack to the second bracket, and so that when the rack is supported on the first bracket the second lever is in the disengaged position and the second cam is open thereby releasing the rack from the second bracket.

20. The medical equipment transport system of claim 19 wherein the second bracket comprises a flange extending from one of the conical pins and the second cam comprises a hook configured to receive the flange to lock the rack to the second bracket, wherein second lever comprises a foot positioned to engage the flange on the tapered bushing on the first bracket so that when the pin on the rack is fully seated in the bushing, the foot on the second lever is pushed toward the disengaged position releasing the rack from the second bracket and when the pin is withdrawn from the bushing, the second lever returns to the engaged position locking the rack to the second bracket.

21. The medical equipment transport system of claim 16 wherein the second latch comprises:
   a second cam pivotally mounted to the rack for movement between closed position and an open position, wherein in the closed position the second cam locks the second bracket to the rack, and wherein in the open position, the second cam is disengaged from the second bracket; and
   a second lever for operating the second cam, the second lever being pivotally mounted to the rack for movement between an engaged position, in which the second cam is closed, and a disengaged position, in which the second cam is open, wherein the second lever is biased towards the engaged position, and wherein the second lever has a first end operatively connected to the second cam to control movement thereof, and a second end engagable with the first bracket so that when the rack is disengaged from the first bracket the second lever is in the engaged position and the second cam is closed thereby locking the rack to the second bracket, and so that when the rack is supported on the first bracket the second lever is in the disengaged position and the second cam is open thereby releasing the rack from the second bracket.

22. The medical equipment transport system of claim 21 wherein the second bracket comprises a flange extending from one of the conical pins and the second cam comprises a hook configured to receive the flange to lock the rack to the second bracket, wherein the first bracket comprises a flange extending from one of the tapered bushings, wherein second lever comprises a foot positioned to engage the flange on the tapered bushing on the first bracket so that when the pin on the frame is fully seated in the bushing, the foot on the second lever is pushed toward the disengaged position releasing the rack from the second bracket and when the pin is withdrawn from the bushing, the second lever returns to the engaged position locking the rack to the second bracket.

23. The medical equipment transport system of claim 1 comprising a self-locking and self-releasing latch assembly adapted to secure the rack alternately to the first and second brackets as the rack is transferred between the patient transport device and the tower.

24. The medical equipment transport system of claim 23 wherein the latch assembly comprises a first latch engagable with the first bracket and a second latch engagable with the second bracket.

25. The medical equipment transport system of claim 24 wherein the first and second latches are independently operable.

26. The medical equipment transport system of claim 25 wherein the first latch comprises:
   a first cam pivotally mounted to the rack for movement between closed position and an open position, wherein in the closed position the first cam locks the first bracket to the rack, and wherein in the open position, the first cam is disengaged from the first bracket; and
   a first lever for operating the first cam, the first lever being pivotally mounted to the rack for movement between an engaged position, in which the first cam is closed, and a disengaged position, in which the first cam is open, wherein the first lever is biased towards the engaged position, and wherein the first lever has a first end operatively connected to the first cam to control movement thereof, and a second end engagable with the second bracket so that when the rack is disengaged from the second bracket the first lever is in the engaged position and the first cam is closed thereby locking the rack to the first bracket, and so that when the rack is supported on the second bracket the first lever is in the disengaged position and the first cam is open thereby releasing the rack from the first bracket.

27. The medical equipment transport system of claim 26 wherein the first bracket comprises a first flange and the first cam comprises a hook configured to receive the first flange to lock the rack to the first bracket, wherein first lever comprises a foot positioned to engage the second bracket so that when the rack is not supported on the second bracket, the first lever is movable toward the engaged position locking the rack to the first bracket and when the rack is supported on the second bracket the first lever returns to the engaged position locking the rack to the first bracket.

28. The medical equipment transport system of claim 27 wherein the second latch comprises:
   a second cam pivotally mounted to the rack for movement between closed position and an open position, wherein in the closed position the second cam locks the second bracket to the rack, and wherein in the open position, the second cam is disengaged from the second bracket; and
   a second lever for operating the second cam, the second lever being pivotally mounted to the rack for movement between an engaged position, in which the second cam is closed, and a disengaged position, in which the second cam is open, wherein the second lever is biased towards the engaged position, and wherein the second lever has a first end operatively connected to the second cam to control movement thereof, and a second end engagable with the first bracket so that when the rack is disengaged from the first bracket the second lever is in the engaged position and the second cam is closed thereby locking the rack to the second bracket, and so that when the rack is supported on the first bracket the second lever is in the disengaged position and the second cam is open thereby releasing the rack from the second bracket.

29. The medical equipment transport system of claim 28 wherein the second bracket comprises a second flange and the second cam comprises a hook configured to receive the second flange to lock the rack to the second bracket, wherein second lever comprises a foot positioned to engage the flange on the first bracket so that when the frame rack is supported on the first bracket the second lever moves toward the disengaged position releasing the rack from the second bracket and when the rack is not supported on the first bracket the second lever moves toward the engaged position locking the rack to the second bracket.

30. The medical equipment transport system of claim 25 wherein the second latch comprises:

a second cam pivotally mounted to the rack for movement between closed position and an open position, wherein in the closed position the second cam locks the second bracket to the rack, and wherein in the open position, the second cam is disengaged from the second bracket; and a second lever for operating the second cam, the second lever being pivotally mounted to the rack for movement between an engaged position, in which the second cam is closed, and a disengaged position, in which the second cam is open, wherein the second lever is biased towards the engaged position, and wherein the second lever has a first end operatively connected to the second cam to control movement thereof, and a second end engagable with the first bracket so that when the rack is disengaged from the first bracket the second lever is in the engaged position and the second cam is closed thereby locking the rack to the second bracket, and so that when the rack is supported on the first bracket the second lever is in the disengaged position and the second cam is open thereby releasing the rack from the second bracket.

31. The medical equipment transport system of claim 30 wherein the second bracket comprises a second flange and the second cam comprises a hook configured to receive the second flange to lock the rack to the second bracket, wherein the first bracket comprises a first flange, wherein second lever comprises a foot positioned to engage the first flange so that when the rack is supported on the first bracket, the foot of the second lever moves toward the disengaged position releasing the rack from the second bracket and when the rack is not supported on the first bracket the second lever returns to the engaged position locking the rack to the second bracket.

32. The medical equipment transport system of claim 1 comprising a self-locking and self-releasing latch assembly adapted to secure the rack alternately to the first and second frame support brackets as the rack is transferred between the patient transport device and the tower, the latch assembly comprising a first latch adapted to lock the rack to the first bracket and a second latch adapted to lock the rack to the second bracket, wherein the first latch remains in the locked position unless the rack is supported substantially by the second bracket, wherein the second latch remains in the locked position unless the rack is substantially supported by the first bracket, and wherein both the first and second latches are released only when the rack is supported on both the first and second brackets.

33. The medical equipment transport system of claim 1 further comprising an adapter configured to be attached to the patient transport device without any structural modification of the device and wherein the first bracket is attachable to the adapter.

34. The medical equipment transport system of claim 1 wherein the tower is mobile.

35. The medical equipment transport system of claim 1 wherein the equipment rack comprises a base and a post assembly removably supportable on the base.

36. The medical equipment transport system of claim 35 wherein the post assembly is pivotally supported on the rack base.

37. The medical equipment transport system of claim 36 wherein the equipment rack base comprises a retractable post assembly pivot control pin operable between a retracted position and an extended position, the post assembly pivot control pin being biased in the extended position, wherein the post assembly comprises a plurality of pin receiving recesses configured to receive the post assembly pivot control in the extended position to retain the post assembly in one of a plurality of selected positions.

38. The medical equipment transport system of claim 37 wherein the rack base comprises a rack base pivot control pin operable between a retracted position and an extended position, the rack base pivot control pin being biased in the extended position, wherein the first bracket comprises a plurality of pin receiving recesses configured to receive the rack base pivot control pin in the extended position to retain the rack base in one of a plurality of selected positions.

39. The medical equipment transport system of claim 36 wherein the rack base comprises a rack base pivot control pin operable between a retracted position and an extended position, the rack base pivot control pin being biased in the extended position, wherein the first bracket comprises a plurality of pin receiving recesses configured to receive the rack base pivot control pin in the extended position to retain the rack base in one of a plurality of selected positions.

* * * * *